(12) United States Patent
Jokela et al.

(10) Patent No.: US 11,046,905 B2
(45) Date of Patent: Jun. 29, 2021

(54) METHOD FOR PRODUCING RENEWABLE FUELS

(71) Applicant: UPM-KYMMENE CORPORATION, Helsinki (FI)

(72) Inventors: Pekka Jokela, Espoo (FI); Liisa Ranta, Tuusula (FI); Timo Lehesvirta, Porvoo (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 24 days.

(21) Appl. No.: 16/399,125

(22) Filed: Apr. 30, 2019

(65) Prior Publication Data

US 2019/0338208 A1     Nov. 7, 2019

(30) Foreign Application Priority Data

May 3, 2018   (FI) ...................... 20185412

(51) Int. Cl.
*C10L 5/44* (2006.01)
*C10G 3/00* (2006.01)
*C10L 1/04* (2006.01)

(52) U.S. Cl.
CPC ................ *C10L 5/447* (2013.01); *C10G 3/42* (2013.01); *C10L 1/04* (2013.01); *C10G 2300/1011* (2013.01); *C10L 2200/0469* (2013.01)

(58) Field of Classification Search
CPC .. C10L 5/447; C10L 1/04; C10G 3/42; C10G 2300/1011
See application file for complete search history.

(56) References Cited

U.S. PATENT DOCUMENTS

| 2004/0235663 | A1 | 11/2004 | Cocking | |
| 2015/0080261 | A1* | 3/2015 | Wigley | A01N 63/00 506/10 |
| 2017/0086402 | A1* | 3/2017 | Meadows-Smith | A01H 1/00 |

FOREIGN PATENT DOCUMENTS

| CN | 101671205 | 3/2010 |
| WO | 8704182 | 7/1987 |
| WO | 9726363 | 7/1997 |
| WO | 03020014 A2 | 3/2003 |
| WO | 2015004329 | 1/2015 |
| WO | 2016016630 | 2/2016 |

(Continued)

OTHER PUBLICATIONS

Oliveira et al., Survival of Endophytic Diazotrophic Bacteria In Soil Under Different Moisture Levels, (2004), Brazilian Journal of Microbiology, 35:295-299 (Year: 2004).*

(Continued)

*Primary Examiner* — Cephia D Toomer
(74) *Attorney, Agent, or Firm* — Cantor Colburn LLP

(57) ABSTRACT

The present invention relates to production of renewable fuels and fuel components from plant oil originating from at least one *Brassica* species, where said *Brassica* species, doped with at least one nitrogen-fixing bacteria, is cultivated to obtain *Brassica* seed oil, and feedstock comprising the *Brassica* seed oil is converted in a converting step, whereby renewable fuel or renewable fuel components are obtained. The invention also relates to a method for reducing nitrate release in renewable fuel production. Further, the invention relates to a method for reducing greenhouse gases in renewable fuel production.

32 Claims, 3 Drawing Sheets

(56) References Cited

FOREIGN PATENT DOCUMENTS

WO     WO2019046968    *   3/2019

OTHER PUBLICATIONS

Basili, M. et al., *Brassica carinata*-derived biodiesel production: economics, sustainability and policies. The Italian case. Journal of Cleaner Production, 2018, vol. 191, pp. 40-47, Available online Apr. 20, 2018.

Cardone, ME. et al., "*Brassica carinata* as an alternative oil crop for the production of biodiesel in Italy: agronomic evaluation, fuel production by transesterification and characterization", Biomass and Bioenergy, 2003, vol. 25, pp. 623-636.

Megawer, E. et al, response of canola (*Brassica napus* L.) to biofertilizers under Egyptian conditions in newly reclaimed soil, International Journal of Agriculture Sciences, 2010, vol. 2, No. (1), pp. 12-17.

Nosheen A. et al., The role of plant growth provoting rhizobacteria on oil yield and biodiesel production of Canola (*Brassica napus* L.). Energy Sources, 2013, Part A, vol. 35, No. 16 pp. 1574-1581.

Nosheen, A. et al., Bioinoculants: a sustainable approach to maxiize the yield of Ethiopian mustard (*Brassica carinat* L. ) under low input of chemical fertilizers Toxicology and Industrial Health, vol. 32, No. 2, Epub. 3013, pp. 1-8, doi: 101177/0748233713498453.

Reay, Dave S. et al., "Global agriculture and nitrous oxide emissions," Nature Climate Change, vol. 2, Jun. 2012; pp. 410-416.

European Search Report for the corresponding European Application No. 19170977; dated Sep. 18, 2019; 3 pages.

Nosheen, A., "Role of Plant Growth Promoting Rhizobacteria and chemical fertilizers on plant growth, oil content and quality of Safflower and Canola and their potential for biodiesel production", a dissertation, Department of Plant Sciences, Faculty of Biological Sciences, 2014; 310 pages.

Jeromela, A. M. et al., "Potential of Legume-*Brassica* Intercrops for Forage Productions and Green Manure: Encouragements from a Temperate Southeast European Environment", Frontiers in Plant Science, vol. 8, Mar. 2017; 8 pages.

* cited by examiner

METHOD FOR PRODUCING RENEWABLE FUELS

CROSS REFERENCE TO RELATED APPLICATIONS

This application claims the benefit of Finnish Patent Application No. 20185412, filed May 3, 2018, which is incorporated by reference herein in its entirety

TECHNICAL FIELD

The invention relates to production of renewable fuels and renewable biofuel components from plant oil originating from at least one *Brassica* species, where said *Brassica* species, doped with at least one nitrogen-fixing (N-fixing) bacteria is cultivated, which nitrogen-fixing bacteria fixes nitrogen from the surrounding environment, whereby plant oil is obtained from the at least one *Brassica* species, and converting the plant oil to renewable fuel or renewable fuel components. The invention also relates to a method for reducing nitrate release in renewable fuel production. Further, the invention relates to a method for reducing greenhouse gases (GHG) in renewable fuel production.

BACKGROUND

Human activities have constantly increased the atmospheric concentration of greenhouse gases (GHG), which absorb and emit radiation within the thermal infrared range. It is estimated that without greenhouse gases the average soil temperature of earth would be −18° C., rather than the present average of +15° C. The primary greenhouse gases in the earth's atmosphere are water vapor, carbon dioxide ($CO_2$), methane ($CH_4$), nitrous oxide ($N_2O$) and ozone ($O_3$).

Each of these gases have characteristic estimated atmospheric lifetime, which measures the time required to restore equilibrium following a sudden increase or decrease in its concentration in the atmosphere. Individual atoms or molecules may be lost or deposited to sinks such as soil, the oceans, and other waters, vegetation or the biological systems, reducing the excess to background concentration. The average time taken to achieve this is the mean lifetime. $N_2O$ has an atmospheric lifetime of 114 years, which is significantly longer than that of $CO_2$ or $CH_4$.

Global warming potential (GWP) depends on both the efficiency of the molecule as a greenhouse gas and its atmospheric lifetime. GWP is measured relative to the same mass of $CO_2$ and evaluated for a specific timescale. $CO_2$ is defined to have a GWP of 1 over all time periods. GWP for $N_2O$ for 20-year time-period is 289 and 100-year time-period is 298. This means that the initial impact is higher, and it increases within the timescale.

Chemical fertilizers, particularly nitrogen containing synthetic fertilizers (N-fertilizers) are heavily used in the agriculture. Input efficiency of N-fertilizers is one of the lowest among the plant nutrients and it contributes substantially to environmental pollution. The crop yields decline from nitrogen (N) addition, whereby increased amounts of N-fertilizers are used. The overuse of N-fertilizers causes serious nitrate pollution, which is a health hazard; nitrate in ground water is a serious health hazard. Further, nitrates and nitrogen compounds originating from N-fertilizers washed to run-offs and surface waters in waterways, such as in lakes and rivers cause eutrophication and pollution; in seas and oceans they cause "dead zones".

Industrial processes from producing N-fertilizers are heavily reliant on fossil fuel, whereby a major proportion of energy supplies are utilized. N-fertilizers are typically manufactured from $N_2$ gas by the Haber-Bosch process where high quantities of $H_2$ gas are used, typically obtained from natural gas, in addition to high amounts of energy for establishing and maintaining high temperature and pressure in the production of ammonia ($NH_3$).

Interest in renewable fuels and renewable fuel production increases constantly. At the same time, much effort is put in the research for providing environmentally sustainable processes and systems where the environmental burden can be reduced significantly.

Despite the ongoing research and development of processes and systems for the renewable fuel production, there is still a need to provide an improved process, where particularly the GHG gases and warming potential caused by said gases can be reduced.

SUMMARY OF THE INVENTION

Disclosed herein is a method for producing renewable fuels and renewable fuel components, where the method comprises the steps, where,
  seeds of at least one plant selected from *Brassica* species are doped with a doping composition comprising at least one nitrogen-fixing bacteria to obtain doped *Brassica* seeds,
  in a first farming season, the doped *Brassica* seeds are planted in soil and a *Brassica* seed crop is harvested,
  the *Brassica* seed crop is treated to obtain *Brassica* seed oil and meal, and
  feedstock comprising the *Brassica* seed oil is converted in a converting step, whereby renewable fuel or renewable fuel components are obtained.

Disclosed herein is also method for reducing nitrate release in renewable fuel production, where the method comprises the steps, where,
  seeds of at least one plant selected from *Brassica* species are doped with a doping composition comprising at least one nitrogen-fixing bacteria to obtain doped *Brassica* seeds,
  in a first farming season, the doped *Brassica* seeds are planted in soil and a *Brassica* seed crop is harvested,
  the *Brassica* seed crop is treated to obtain *Brassica* seed oil and meal, and
  feedstock comprising the *Brassica* seed oil is converted in a converting step, whereby renewable fuel or renewable fuel components are obtained.

Disclosed herein is also method for reducing greenhouse gases (GHG) in renewable fuel production, where the method comprises the steps, where,
  seeds of at least one plant selected from *Brassica* species are doped with a doping composition comprising at least one nitrogen-fixing bacteria to obtain doped *Brassica* seeds,
  in a first farming season, the doped *Brassica* seeds are planted in soil and a *Brassica* seed crop is harvested,
  the *Brassica* seed crop is treated to obtain *Brassica* seed oil and meal, and
  feedstock comprising the *Brassica* seed oil is converted in a converting step, whereby renewable fuel or renewable fuel components are obtained.

Optionally, the methods further comprise growing in a soil, in a farming season preceding or succeeding the first farming season, at least one plant of *Brassica* species, grain species or forage species, harvesting the *Brassica* crop, grain crop or forage crop, and leaving at least part of plant biomass in and/or on the soil.

Seeds of the plant of the *Brassica* species used in the farming season preceding or succeeding the first farming season may be doped with a doping composition comprising at least one nitrogen-fixing bacteria, or alternatively said seeds are not doped.

The plant of the *Brassica* species used in the farming season preceding or succeeding the first farming season may be the same *Brassica* species, which is used in the first farming season, or alternatively it may be a different *Brassica* species.

In an embodiment, the plant species used in the farming season preceding or succeeding the first farming season, is grown or cultivated in a rotating manner by alternating it with the plant of *Brassica* species, doped with at least one nitrogen-fixing bacteria and used in first farming season.

Optionally, the methods comprise leaving the soil fallow for one or more farming seasons.

In the methods, the doping, the planting of the doped *Brassica* seeds and following growing/farming, the treating of the *Brassica* seed crop and the converting may be carried out by one or more producers, different from the one carrying out the converting, or they may be carried out by the same producer.

Optionally, the converting or converting step comprises at least one pretreatment step of *Brassica* seed oil.

In an embodiment the pretreatment may comprise degumming of the *Brassica* seed oil to separate the degumming residue from the seed oil. Said degumming residue comprises phospholipids.

The degumming residue resulting from the degumming step is optionally composted for facilitating the uptake of nutrients. Thereafter, it may be used as a component in a fertilizer or as a fertilizer, which may be spread to soil.

The obtained renewable fuels and renewable fuel components may be used as transportation fuels, components in transportation fuels and as industrial chemicals.

Characteristic features of said methods are presented in the appended claims.

Definitions

The term "renewable fuel" refers here to a fuel made from raw material of biological origin, or from renewable feedstock.

Raw material of biological origin or renewable feedstock is produced through biological processes, such as agriculture, anaerobic digestion, etc. rather than crude mineral oil produced by geological processes such as those involved in the formation of fossil fuels.

Renewable fuel comprises hydrocarbon fractions and/or fatty acid ester fractions obtained by processing of renewable feedstocks.

The term "renewable fuel component" refers here to hydrocarbon fractions, fatty acid ester fractions and components comprising said fractions, obtained by processing of renewable feedstocks.

The term "growing" refers here to farming, cultivation, culturing, crofting and cropping.

The term "growing season" refers here to the period of the year when crops and other plants grow successfully i.e. the time period when the weather allows plants to grow. For example, in tropical regions, where it is warm year-round, the growing season can last the entire year.

The term "summer farming season" or "normal farming season" or "summer growing season" refers here to the growing or culturing season, which is considered as "summer season" in the region where the growing of the plant takes place.

The term "winter season" or "winter farming season" or "winter growing season" refers here to the growing or culturing season, which is considered as "winter season" in the region where the growing of the plant takes place.

The length of the growing season varies for different regions and different plants. Most crops need a growing season of at least 90 days. Typically, the length of the growing season of a crop is from 5 to 10 months, suitably from 5 to 8 months, however some plant varieties need only 2-5 months. In temperate regions, which have warm summers and cold winters, the length of the growing season depends mostly on temperature. Typically, the farther away a place is from the Equator, the shorter the growing season.

There are two ways to define the growing season. In temperate regions, the growing season is usually calculated by the average number of days between the last frost in spring and the first severe frost in autumn. Specifically, it is defined as the period of time between the average last date at which the overnight low temperature drops below 0° C. in the spring and the average date at which the overnight low first drops down below 0° C. in the fall. In most areas of Europe, the growing season is defined as the average number of days a year with a 24-hour average temperature of at least +5° C. This is typically from April until October or November, although this varies considerably with latitude and altitude. The growing season can also be determined by the average number of days that the temperature rises high enough for a particular crop to sprout and grow. This measurement varies depending upon the crop.

The term "cultivation of plants in a rotating manner" refers here to "crop rotation". Said term also refers to sequential cropping. Crop rotation is the practice of growing a series of dissimilar or different types of crops in the same area in sequenced seasons. Crop rotation helps in reducing soil erosion and increases soil fertility and crop yield. Crop rotation may also improve soil structure and fertility by increasing biomass from varied root structures.

In agriculture, the term "multiple cropping" is the practice of growing two or more crops in the same piece of land in different growing seasons. It is a form of polyculture. It can take the form of "double-cropping", in which a second crop is planted after the first has been harvested, or "relay cropping", in which the second crop is started amidst the first crop before it has been harvested. The second crop may be harvested, or it may be left unharvested whereby the whole plants are left in the field.

The term "meal" refers here to the edible part of a grain or pulse, resulting from separation of oil, used mainly as animal feed or fodder.

The term "tillage" refers her to the practice of plowing soil to prepare for planting or for nutrient incorporation or for pest control. Tillage may vary in intensity from conventional to no tillage. Tillage is typically used for improving productivity by warming the soil, incorporating fertilizer and controlling weeds.

The term "greenhouse gas" or "GHG" refers here to a gas in atmosphere that adsorbs and emits radiation within the thermal infrared range. This process is the fundamental cause of the greenhouse effect. The primary greenhouse gases in Earth's atmosphere are water vapor ($H_2O$), carbon dioxide ($CO_2$), methane ($CH_4$), nitrous oxide ($N_2O$), ozone ($O_3$), chlorofluorocarbons (CFCs) and hydrofluorocarbons (HCFCs and HFCs).

The term "carbon balance" refers here to the difference between carbon gains and losses of an ecosystem at any point in time.

The term "grain species" refers here to plants selected from the group consisting of wheat, rye, barley, oats, rice, sorghum, maize, millet, vegetables (such as potato or tomato), buckwheat, quinoa, fonia, teff, spelt and edible oil seed species such as sunflower. The term "grain species" includes here particularly edible grain-producing plants, edible oil seed plants and vegetables.

The term "forage species" refers here to annual or biennial crop species, which are grown to be utilized by livestock. Examples or forage species are grasses.

The term "fallow" refers here to cultivated farmland, which is left unplowed and unseeded during one or more farming seasons.

The term "nitrogen fixation" or "nitrogen fixing" refers here to a process by which nitrogen in the surrounding environment and/or atmosphere is converted into ammonia ($NH_3$) or other nitrogen containing molecules available to living organisms. Nitrogen fixation is carried out naturally in the soil by nitrogen fixing bacteria. Some nitrogen-fixing bacteria have symbiotic relationships with some plant groups.

The term "nitrogen fixation by plants" refers here to a process that changes $N_2$ into biologically useful $NH_3$, mediated by N-fixing bacteria in plants.

In some plants, the bacteria live in the plant tissue, such as root tissue or in small growths on the roots called nodules. The plant supplies all the necessary nutrients and energy for the bacteria. The degree of plant's ability to fix nitrogen varies. Peanuts, soybeans and fava beans are good nitrogen fixers. Usually additional nitrogen fertilization is not needed. In fact, the plant often slows or shuts down the nitrogen fixation process, if an excessive amount of nitrogen is applied. Nearly all the fixed nitrogen is used directly by the plant. Eventually, most of the nitrogen returns to the soil when roots, leaves, and fruits of the plant e.g. the legume are left in or on the soil, die and decompose. Typically, at least part of the nitrogen remains in the soil even when the crop (fruit) is harvested. The remaining plant parts also return fertilizing components to the soil.

The term "root nodule" or "nodule" refers here to a swelling on the root of a plant that contains bacteria, capable of nitrogen fixation. Root nodules occur on the roots of plants that associate with symbiotic nitrogen-fixing bacteria, such as of the genus *Rhizobium*. Under nitrogen-limiting conditions, capable plants form a symbiotic relationship with a host-specific strain of the bacteria. Within nodules, $N_2$ gas from the surrounding environment or atmosphere is converted into $NH_3$.

The term "nodulation factor" or "nod factor" refers here to a signaling molecule produced by N-fixing bacteria during the initiation of nodules on the roots of plants. Nodulation is controlled by nodulation (nod) genes. The nod genes encode enzymes involved in the synthesis of Nod factors that induce morphological changes in plant roots. Plants release nod-factor inducing agents such as flavonoids from their roots, which trigger the production of Nod factors by the bacteria. Nod factors are lipochito-oligosaccharides and have three to five N-acetyl-glucosamines. A number of biochemical and morphological changes are initiated, when the nod factor is sensed by the root. Cell division is triggered in the root to create the nodule, and the root hair growth is redirected to wind around the bacteria multiple times until it fully encapsulates one or more bacteria. The bacteria encapsulated form a microcolony. From this microcolony, the bacteria enter the developing nodule through an infection thread, which grows through the root hair into the basal part of the epidermis cell, and onwards into the root cortex; they are then surrounded by a plant-derived membrane and differentiate into bacteroids that fix nitrogen. Effective nodulation takes place approximately four weeks after planting a crop. The size, and shape of the nodules depends on the planted crop.

The term "N-fixing bacteria" or "nitrogen fixing bacteria" refers here to the bacteria responsible for nitrogen fixation. Such bacteria are called diazotrophs; they encode nitrogenase, the enzyme complex that catalyzes the conversion of nitrogen ($N_2$) gas to ammonia ($NH_3$). Various types of associations and/or interactions occur between diazotrophs and their host plants. Two kinds of nitrogen-fixing bacteria exist. Symbiotic bacteria include *Rhizobium*, typically associated with leguminous plants; *Frankia*, typically associated with certain dicotyledonous species (actinorhizal plants); and certain *Azospirillum* species, typically associated with cereal grasses. Free-living (nonsymbiotic) bacteria, include the cyanobacteria (or blue-green algae) *Anabaena* and *Nostoc* and genera such as *Azotobacter, Beijerinckia*, and *Clostridium*. Members of *Rhizobium* genera are capable of forming endosymbiotic interactions with plants. These bacteria have the ability to fix nitrogen into a form that plants can utilize. The enzyme that is used for this process is nitrogenase and it can reduce atmospheric $N_2$ to $NH_3$ at normal temperatures and atmospheric pressure.

The N-fixing bacteria may be accompanied with other symbiotic microbes, such as other bacteria, fungi etc.

The term "*Brassica* species" refers here to the plants of a genus *Brassica* and the genus *Sinapis*, in the mustard family (Brassicaceae). *Brassica* species include plant species such as *Brassica juncea* (brown mustard); *Brassica carinata* (*Carinata*, Ethiopian mustard); *Brassica oleracea* (cabbage); *Brassica nigra* (black mustard); *Brassica rapa*, especially *Brassica rapa* subsp. *oleifera* (field mustard), *Brassica napus*, especially *Brassica napus* subsp. *oleifera* (oilseed rape); *Sinapis hirta; Sinapis alba*; and subspecies, cultivars, varieties and hybrids thereof.

The term "doping" refers here to inoculation or treatment of seeds with doping composition or exposing of seeds to inoculum comprising the doping composition.

The term "doping with nitrogen-fixing bacteria" refers here to treatment of plant seeds with a doping composition comprising at least one nitrogen-fixing bacteria.

The term "plant biomass" refers here to at least one of roots, crowns, leaves, stems and seeds.

The term "nitrogen fertilizer" or "N-fertilizer" refers here to synthetic or natural (manure) fertilizer or a combination thereof, containing nitrogen.

The term "germinant" refers here to a substance or compound that induces microbial spore germination, e.g. germination of fungal or bacterial spore. Non-limiting examples of germinants include lactate, lactose, bicarbonate, fructose, glucose, mannose, galactose, alanine, asparagine, cysteine, glutamine, norvatine, serine, threonine, valine, glycine, inosine, taurocholate, carbonate compounds and carbon dioxide and combinations thereof.

The term "nitrate release" refers here to a process or occurrence wherein nitrates and/or nitrogen compounds originating from N-fertilizers are washed to run-offs and surface waters in waterways, such as in lakes and rivers causing e.g. eutrophication and pollution.

The term "pretreatment of *Brassica* seed oil" refers here to at least one of physical refining and chemical refining of seed oil, where said refining may comprise at least one of degumming, bleaching, hydrolysis, soap stock splitting, deacidification, alkali neutralization, cold neutralization, micella refining, and deodorization, and any combinations thereof. The converting or converting step may comprise optional pretreatment of *Brassica* seed oil.

The term "degumming" refers here to the removal of gums, particularly hydratable and non-hydratable phosphatides from a material e.g. from plant oils. Degumming is typically applied to plant oils that contain phospholipids in significant amounts. Several degumming methods, such as water degumming, acid degumming, deep degumming utilizing agents able to chelate particularly Fe, Ca and Mg, enzymatic degumming, and alkali refining are available for removal of gum from plant oils. Water degumming consists of treating heated natural oil with water, followed by centrifugal separation. The separated phospholipids are rather waxy or gummy solids. These gums consist mainly of phosphatides, but they may also contain entrained oil and meal particles.

The term "degumming residue" refers here to a residue resulting from a degumming process, and the residue comprises separated phospholipids and other solids.

The term "converting" or "converting step" refers here to at least one of hydroprocessing, deoxygenation, and transesterification.

The term "hydroprocessing" refers here to catalytic processing of feedstock by all means of molecular hydrogen. Hydroprocessing includes hydrogenation, which means here saturation of carbon-carbon double bonds by means of molecular hydrogen under the influence of a catalyst, hydrocracking (HC), which refers to catalytic decomposition of organic hydrocarbon materials using molecular hydrogen at high pressures, hydrodewaxing (HDW), which refers to catalytic treatment of organic hydrocarbon materials using molecular hydrogen at high pressures to reduce the wax and/or the content of high carbon number hydrocarbons by isomerization and/or cracking. Said hydroprocessing also includes hydroisomerization (HI), ring opening and saturation of aromatic compounds. Said hydroprocessing further includes hydrodearomatization (HDA), which refers to catalytic treatment of organic hydrocarbon materials using molecular hydrogen at high pressures for converting aromatic compound to non-aromatic compounds. Said hydroprocessing also includes hydrotreatment. One or more of the above cited reactions may take place in hydroprocessing.

The term "hydrotreatment" refers here to a catalytic process, which removes oxygen from organic oxygen compounds as water (hydrodeoxygenation, HDO), sulfur from organic sulfur compounds as dihydrogen sulfide (hydrodesulfurisation, HDS), nitrogen from organic nitrogen compounds as ammonia (hydrodenitrogenation, HDN), halogens, for example chlorine from organic chloride compounds as hydrochloric acid (hydrodechlorination, HDCl), by the means of molecular hydrogen.

Also, the terms "hydroprocessing" or "hydrotreatment" refer here to processes where feedstock comprising plant seed oil is converted to obtain renewable fuel or renewable fuel components.

The term "deoxygenation" refers here to the removal of oxygen from organic molecules, such as carboxylic acid derivatives, alcohols, ketones, aldehydes or ethers. Catalytic deoxygenation can proceed by decarboxylation and/or decarbonylation, in liquid or in gas phase.

The term "decarboxylation" and/or "decarbonylation" refers here to the removal of carboxyl oxygen as $CO_2$ (decarboxylation) or as CO (decarbonylation), with or without the influence of molecular hydrogen.

The term transesterification means here changing one ester group to another ester group.

The term "transportation fuels" refers here to fractions or cuts or blends of hydrocarbons having distillation curves standardized for fuels, such as for diesel fuel (middle distillate from 160 to 380° C., EN 590), gasoline (40-210° C., EN 228), aviation fuel (160 to 300° C., ASTM D-1655 jet fuel), kerosene, naphtha, etc.

The term "transportation fuels" includes here also fractions, cuts and blends of fatty acid esters meeting the requirements standardized for fuels, such as EN 14214 for FAME (fatty acid methyl esters).

Transportation fuels include here renewable fuels comprising hydrocarbon fractions and/or fatty acid ester fractions and components obtained by processing of renewable feedstocks.

Liquid fuels comprise mixtures of hydrocarbons or fatty acid esters, having distillation curves standardized for fuels.

DETAILED DESCRIPTION

Figure 1:
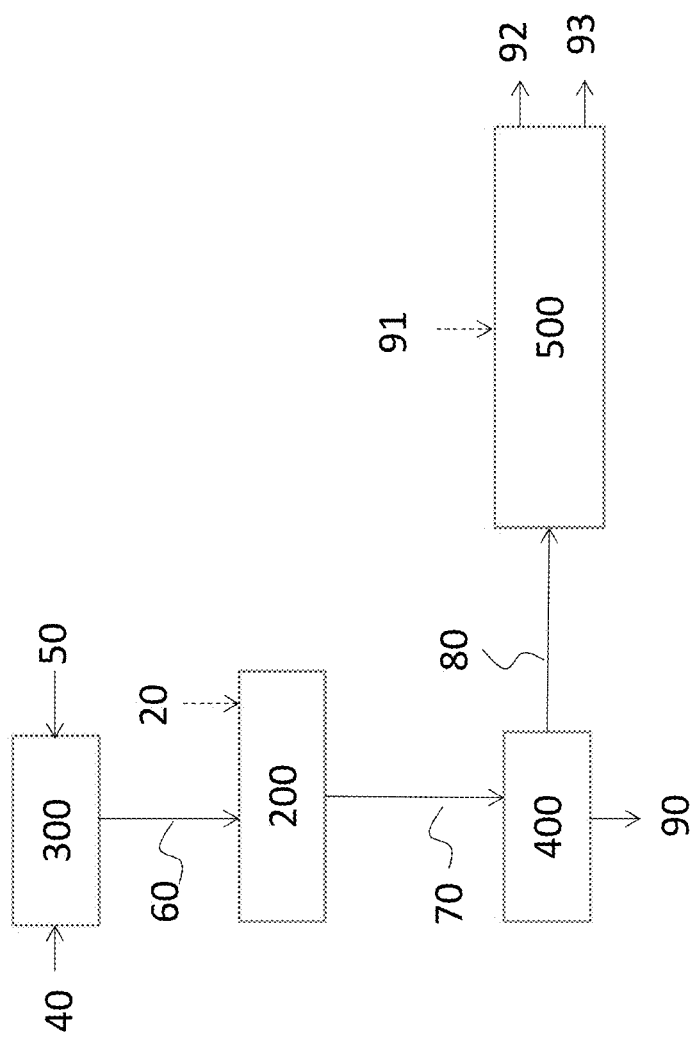
FIG. 1 presents an embodiment of the method.

It should be understood that, although an illustrative implementation of one or more embodiments are provided below, the disclosed methods and processes can be implemented using any number of techniques. The disclosure should in no way be limited to the illustrative implementation, drawings, or techniques illustrated below, including the exemplary designs describe herein, but can be modified within the scope of the appended claims along with their full scope of equivalents.

Disclosed herein is a method for producing renewable fuels and renewable fuel components, where the method comprises the steps, where, seeds of at least one plant selected from *Brassica* species are doped with a doping composition comprising at least one nitrogen-fixing bacteria to obtain doped *Brassica* seeds, in a first farming season, the doped *Brassica* seeds are planted in soil and a *Brassica* seed crop is harvested, the *Brassica* seed crop is treated to obtain *Brassica* seed oil and meal, and feedstock comprising the *Brassica* seed oil is converted in a converting step whereby renewable fuel or renewable fuel components are obtained.

Disclosed herein is also method for reducing nitrate release in renewable fuel production, where the method comprises the steps, where, seeds of at least one plant selected from *Brassica* species are doped with a doping composition comprising at least one nitrogen-fixing bacteria to obtain doped *Brassica* seeds, in a first farming season, the doped *Brassica* seeds are planted in soil and a *Brassica* seed crop is harvested, the *Brassica* seed crop is treated to obtain *Brassica* seed oil and meal, feedstock comprising the *Brassica* seed oil is converted in a converting step, whereby renewable fuel or renewable fuel components are obtained.

Disclosed herein is also method for reducing greenhouse gases (GHG) in renewable fuel production, where the method comprises the steps, where, seeds of at least one plant selected from *Brassica* species are doped with a doping composition comprising at least one nitrogen-fixing bacteria to obtain doped *Brassica* seeds, in a first farming season, the doped *Brassica* seeds are planted in soil and a *Brassica* seed crop is harvested, the *Brassica* seed crop is treated to obtain *Brassica* seed oil and meal, feedstock comprising the *Brassica* seed oil is converted in a converting step, whereby renewable fuel or renewable fuel components are obtained.

In the methods, the *Brassica* seed crop is treated to obtain *Brassica* seed oil and meal, where said meal refers to *Brassica* meal.

Optionally, the methods further comprise growing in a soil, in a farming season preceding or succeeding the first farming season, at least one plant of *Brassica* species, grain species or forage species, harvesting the *Brassica* crop, grain crop or forage crop, obtained in the farming season preceding or succeeding the first farming season, and leaving at least part of plant biomass in and/or on the soil.

Seeds of the plant of the *Brassica* species used in the farming season preceding or succeeding the first farming season may be doped with a doping composition comprising at least one nitrogen-fixing bacteria, or alternatively they are not doped.

The plant of the *Brassica* species used in the farming season preceding or succeeding the first farming season may be the same *Brassica* species, which is used in the first farming season, or alternatively it may be a different *Brassica* species.

In an embodiment, the plant species used in the farming season preceding or succeeding the first farming season, is grown or cultivated in a rotating manner by alternating it with the plant of *Brassica* species, doped with at least one nitrogen fixing bacteria and used in first farming season.

The grain species include here grain-producing plants, oil seed plants and vegetables, useful as food crop i.e. fit for human consumption.

In an embodiment, the grain species is selected from the group consisting of wheat, rye, barley, oats, rice, sorghum, maize, millet, vegetables (such as potato or tomato), buckwheat, quinoa, fonia, teff, spelt and edible oil seed plant species such as sunflower.

The forage species is selected from grasses.

In an embodiment, the at least one plant of *Brassica* species, grain species or forage species is grown or cultivated in a rotating manner by alternating the plant of *Brassica* species, grain species or forage species with the plant of at least one *Brassica* species, which *Brassica* species is doped with at least one nitrogen fixing bacteria.

In the methods, the doping, the planting of the doped *Brassica* seeds and following growing/farming, the treating of the *Brassica* seed crop and the converting, and the optional farming in the farming season preceding or succeeding the first farming season, may be carried out by one or more producers, different from the one carrying out the converting, or they may be carried out by the same producer.

In an embodiment, at least one plant of forage species or grain species is farmed in the season preceding or succeeding the first farming season.

In an embodiment, the plant of *Brassica* species, forage species or grain species may comprise at least two different plant species, which are grown in the farming season preceding or succeeding the first farming season. Both crops may be harvested, or only one crop may be harvested, or both crops may be left in the field.

Optionally, the methods comprise leaving the soil fallow for one or more farming seasons.

The first farming season may be summer farming season or winter farming season.

The farming season preceding or succeeding the first farming season may be summer farming season or winter farming season.

In an embodiment, the first farming season is summer farming season and the farming season preceding or succeeding the first farming season is winter farming season.

In another embodiment, the first farming season is winter farming season and the farming season preceding or succeeding the first farming season is summer farming season Preferably the farming season preceding or succeeding the first farming season is different from the first farming season.

The farming season is selected based on region where the farming is carried out and based on the plant species which are cultivated.

The farming may be carried out in continents or regions or countries, where the farming of the plant selected from *Brassica* species is suitable, particularly in view of the growing seasons. Suitable countries are for example Uruguay, Argentina, Brazil, Italy, France, Greece, Spain, Portugal, China, Australia etc.

In an embodiment, the doped *Brassica* seeds are planted and farmed in the first farming season, which is the winter farming season, when the farming is carried out in South America, particularly in Uruguay. The optional farming of another crop in the farming season preceding or succeeding the first farming season, takes place in this case in summer farming season.

Optionally, the converting or converting step comprises at least one pretreatment step of *Brassica* seed oil.

In an embodiment the pretreatment may comprise degumming of the *Brassica* seed oil to separate the seed oil from degumming residue. Said degumming residue comprises phospholipids.

The degumming residue resulting from the degumming step is optionally composted for facilitating the uptake of nutrients. Thereafter, it may be used as a component in a fertilizer or as a fertilizer, which may be spread to soil.

Greenhouse gas balance is an important issue in renewable fuel production. Reduced greenhouse gas (GHG) emissions are among the goals of policy measures to support renewable fuel production. The greenhouse gas balance in renewable fuel production is the result of a comparison between all emissions of greenhouse gases throughout the production phases, use of a renewable fuel and all the greenhouse gases emitted in producing, when using the equivalent energy amount of the respective fossil fuel. Improving the greenhouse gas balance plays an important role in renewable fuel production, targeting to emission reduction in transport. Greenhouse gases from originating from agricultural activities, such as fertilization, have big effect on the greenhouse gas balance.

Impact of reduced use of nitrogen fertilizers, particularly synthetic nitrogen fertilizers, has great impact on GHG reduction. When the use of synthetic nitrogen fertilizers in the culture of plants for producing plant oil for renewable fuel production is reduced to half of the typical consumption level, the GHG emissions, particularly $N_2O$, over the whole renewable fuel value chain are reduced by over 15%. Similarly, when no synthetic nitrogen fertilizers are used, the GHG emissions over the whole renewable fuel value chain are reduced by over 30%, compared to the theoretical maximum GHG release.

Improving the greenhouse gas balance plays an important role in renewable fuel production, targeting to emission reduction in transport. Significant reduction of the GHG gases, particularly $N_2O$, can be achieved with the present methods.

The seeds of *Brassica* species are doped with a doping composition comprising at least one N-fixing bacteria, prior to farming/culture of said *Brassica* species, where said bacteria is able to fix nitrogen from the environment, particularly atmosphere. Thus, no added synthetic nitrogen fertilizer or optionally only a minor amount of added synthetic nitrogen fertilizer is required. *Brassica* seed crops with improved overall yields are obtained, whereby significantly reduced amounts of synthetic nitrogen fertilizers, if any are used. The *Brassica* seed crop is treated to obtain *Brassica* seed oil, which is converted to renewable fuels or renewable fuel components, such as fatty acid esters or hydrocarbons.

The nitrate release can be reduced 60%, even 80% in the overall renewable fuel production, when the present methods are used. When no synthetic or additional natural nitrogen fertilizer, such as manure is used, a reduction close to 100% may be reached, particularly in the first farming season.

Crop rotation provides an additional advantage in the presently disclosed methods, where the advantage comes from rotating the *Brassica* species grown from seeds doped with nitrogen-fixing bacteria in the first farming season, and the plant species in the farming season preceding or succeeding the first farming season.

Another advantage is that cultivating *Brassica* species improves the growth and increases crop yield of the plant in the next farming season.

A further advantage is provided when a *Brassica* species is farmed in the farming season preceding or succeeding the first farming season, because also the *Brassica* seed oil harvested from this crop can be utilized in the production of renewable fuels and fuel components.

The doping of the seeds of the plant of *Brassica* species enhances collecting available nitrogen from the soil, air and atmosphere, without nodules on their root structure. When the *Brassica* seed crop is harvested, the biomass of uncollected roots and plant parts breaks down, making the stored nitrogen available to future crops.

In FIG. 1 an embodiment of the process is presented where seeds of a plant selected from *Brassica* species (40) are doped with a doping composition (50) comprising at least one N-fixing bacteria in doping step (300) to obtain doped *Brassica* seeds (60). The doped *Brassica* seeds (60) are subjected to farming in a first farming season (200), where said seeds (60) are planted in a soil, optionally in the presence of a fertilizer (20). *Brassica* seed crop (70) is harvested and plant biomass, roots, crowns and plant residues from the *Brassica* plant are left in/on the soil, for use in the next farming season. Said seed crop (70) is treated in treating step (400) whereby *Brassica* seed oil (80) is separated from *Brassica* press cake (90). *Brassica* seed oil (80) is converted in a converting step (500), optionally in the presence of hydrogen (91), whereby at least one effluent (92, 93) comprising renewable fuel or renewable fuel components is obtained.

The optional fertilizer (20) may comprise one or more of synthetic or natural (manure) nitrogen fertilizers, press cake (90) (or meal) obtained from pressing (400) of *Brassica* seeds (70). The press cake may be subjected to composting prior to fertilizer use. Alternatively, the press cake may be used as animal feed etc.

In a preferable embodiment, no additional synthetic nitrogen fertilizer is used. In another preferable embodiment, no additional synthetic or natural nitrogen fertilizer is used.

Figure 2:
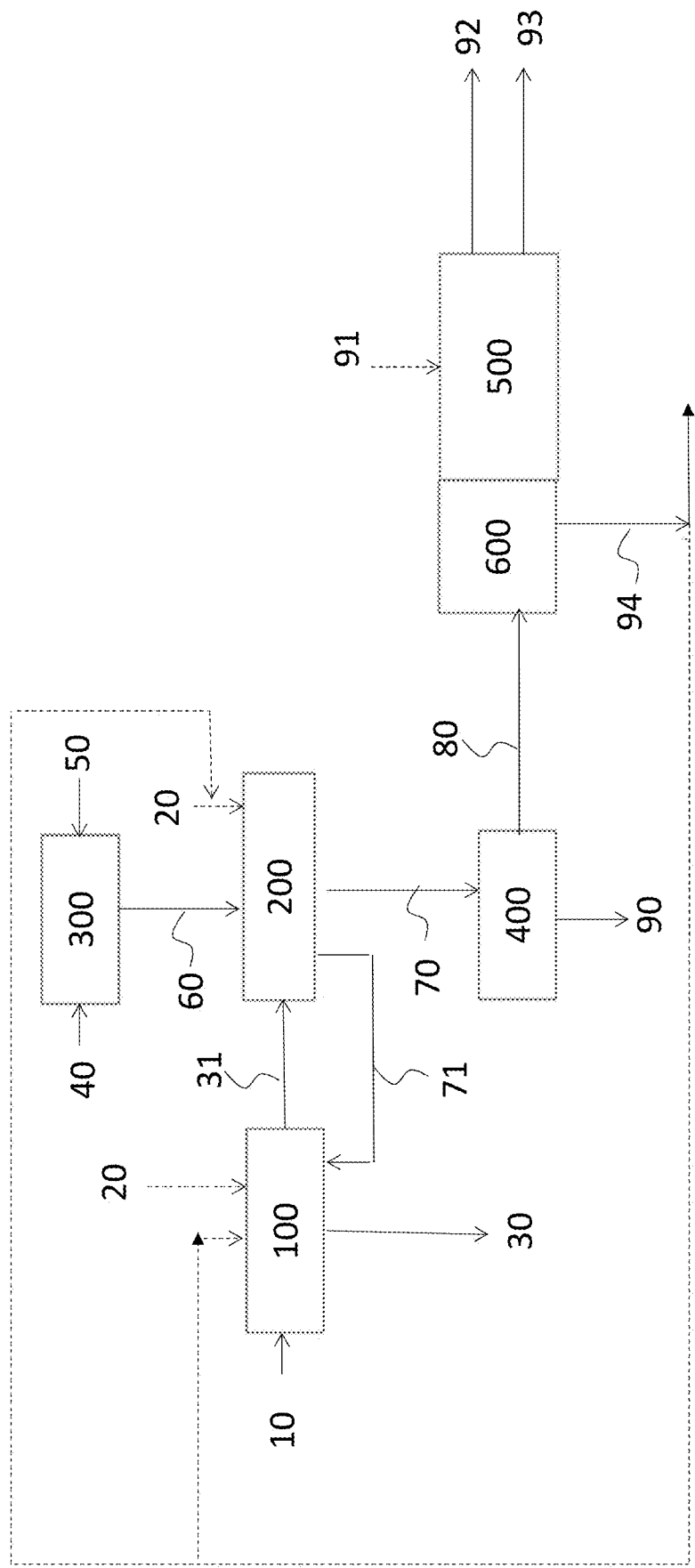
FIG. 2 presents another embodiment of the method.

In FIG. 2 another embodiment of the process is presented where seeds of at least one grain species are farmed in a farming season preceding the first farming season. Seeds of at least one grain species such as wheat (10) are subjected to farming in a farming season (100), optionally in the presence of degumming residue (94) obtained from pretreating (600) of *Brassica* seed oil (80). Optionally, a fertilizer (20) may additionally be used. Grain crop (30) is obtained and it may be used for example for human or animal nutrition. Roots and/or part of other plant biomass from the grain plant (31), such as crowns and plant residues, are left in or on the soil.

Seeds of a plant selected from *Brassica* species (40) are doped with a doping composition (50) comprising N-fixing bacteria in doping step (300) to obtain doped *Brassica* seeds (60). The doped *Brassica* seeds (60) are subjected to farming in a first farming season (200), where said seeds (60) are planted in the soil comprising at least part of the plant biomass (31), optionally in the presence of a fertilizer (20). *Brassica* seed crop (70) is obtained, and plant biomass (71) e.g. roots, crowns and plant residues are left in/on the soil, for use in the next farming season. Said seed crop (70) is treated in a treating step (400) whereby *Brassica* seed oil (80) is separated from *Brassica* press cake (90) (or meal). *Brassica* seed oil (80) is directed to converting step (500) comprising a pretreating step (600), such as degumming step, where degumming residue (94) is separated from the seed oil. The seed oil is converted, optionally in the presence of hydrogen (91), whereby at least one effluent (92, 93) comprising renewable fuel components is obtained.

The optional fertilizer (20) may comprise one or more of synthetic or natural (manure) nitrogen fertilizers, press cake (90) (or meal) obtained from pressing (400) of *Brassica* seeds (70). The press cake may be subjected to composting prior to fertilizer use. Alternative the press cake may be used as animal feed etc.

Figure 3:
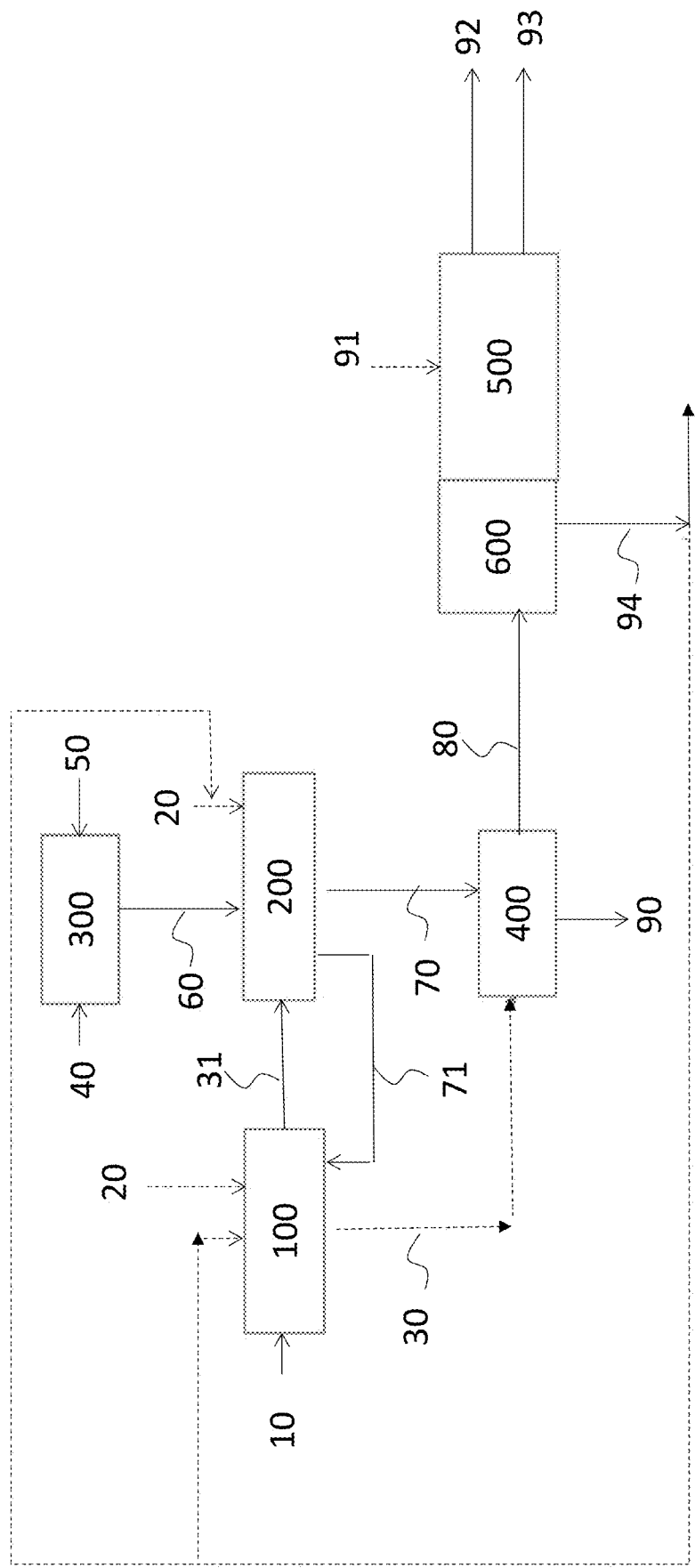
FIG. 3 presents another embodiment of the method.

In FIG. 3 another embodiment of the process is presented. Seeds of at least one *Brassica* species, where seeds are not doped, are farmed in a farming season (100) preceding the first farming season (200). Seeds of at least one *Brassica* species (10), different from the *Brassica* species farmed in the first farming season and not doped, are subjected to farming in a farming season (100), optionally in the presence of degumming residue (94) obtained from pretreating (600) of *Brassica* seed oil (80). Optionally, a fertilizer (20) may additionally be used. *Brassica* seed crop (30) obtained in the farming season (100) preceding the first farming season may optionally be directed to the treating step (400), or it may be used for example for human or animal nutrition. Roots and/or part of other plant biomass from the grain plant (31), such as crowns and plant residues, are left in or on the soil.

Seeds of a plant selected from *Brassica* species (40) are doped with a doping composition (50) comprising N-fixing bacteria in doping step (300) to obtain doped *Brassica* seeds (60). The doped *Brassica* seeds (60) are subjected to farming in a first farming season (200), where said seeds (60) are planted in the soil comprising at least part of the plant biomass (31), optionally in the presence of a fertilizer (20). *Brassica* seed crop (70) is obtained, and plant biomass (71)

e.g. roots, crowns and plant residues are left in/on the soil, for use in the next farming season. Said seed crop (70) is treated in a treating step (400) whereby *Brassica* seed oil (80) is separated from *Brassica* press cake (90) (or meal). *Brassica* seed oil (80) is directed to converting step (500) comprising a pretreating step (600), such as degumming step, where degumming residue (94) is separated from the seed oil. The seed oil is converted, optionally in the presence of hydrogen (91), whereby at least one effluent (92, 93) comprising renewable fuel components is obtained.

The optional fertilizer (20) may comprise one or more of synthetic or natural (manure) nitrogen fertilizers, press cake (90) (or meal) obtained from pressing (400) of *Brassica* seeds (70). The press cake may be subjected to composting prior to fertilizer use. Alternative the press cake may be used as animal feed etc.

The use of the degumming residue as fertilizer, which degumming residue has optionally been composted, reduces also the need for phosphorus containing synthetic fertilizers. Typically, fertilizers comprising one or more of K, P, Ca and S are used, depending of the requirements of the plant and soil.

Farming

In a first farming season the doped *Brassica* seeds are planted in the soil. Typically, the *Brassica* plant emerges between approximately 4-20 days after planting. After emergence, seedling stage occurs with leaves, following with bolting stage where plant produces an elongated shoot with buds at end. Flowers appear within days of bolting and plant continues to produce new flowers while the main stem continues to grow. Flowering stage starts after bolting, depending on planting date, plant variety and prevailing weather conditions. During this stage, both pods and flowers are present. During flowering pollination occurs and pods start to fill. Maturity stage begins when seed is fully formed. When the crop has reached maturity, the seeds are harvested. Harvesting is conducted with any typical oil-seed harvesters. During crop growing period, conventional fertilizers containing no nitrogen or reduced amounts of nitrogen may be used for ensuring adequate nutrients for crop growth.

In an embodiment, in a farming season preceding or succeeding the first farming season, at least one plant of *Brassica* species, forage species or grain species may be farmed in an analogous manner as described above. Harvesting is conducted with any typical harvesters suitable for the selected plant species. During crop growing period, conventional fertilizers containing no nitrogen may be used for ensuring adequate nutrients for crop growth.

In an embodiment, the plant of *Brassica* species, forage species or grain species may comprise at least two different plant species, which are grown in the farming season preceding or succeeding the first farming season. Both crops may be harvested, or only one crop may be harvested, or both crops may be left in the field.

The doped *Brassica* seeds are retrieved by doping seeds of *Brassica* species with a doping composition comprising at least one N-fixing bacteria.

In a preferable embodiment, no additional nitrogen fertilizer is used.

Roots and suitably at least part of other plant biomass, such as crowns and plant residues, are left in or on the soil.

Tillage may be used, or alternatively no tillage is used, depending on the type of soil, growing conditions etc. Tillage may vary in intensity from conventional to no tillage.

After harvesting the plant crop, at least part of the plant biomass is left in and/or on the soil, whereby at least part of the nutrients fixed during the farming seasons returns to the soil. In an embodiment, the plant biomass, which is left on and/or in the soil comprises roots, crowns, stems and leaves.

Eventually, a major part of the nutrients may return to the soil when roots, leaves, and fruits of the plant die and decompose. Typically, at least part of the nutrients remains in the soil even when the crop is harvested. The remaining plant parts also return other fertilizing components to the soil.

The plant/seeds of the *Brassica* species is/are selected from plants of the genus *Brassica* and genus *Sinapis* in the mustard family (Brassicaceae).

The genus *Brassica* includes species such as *Brassica juncea* (brown mustard); *Brassica carinata* (Ethiopian rape); *Brassica nigra* (black mustard); *Brassica rapa*, especially *Brassica rapa* subsp. *oleifera* (field mustard), *Brassica napus*, especially *Brassica napus* subsp. *oleifera* (oil-seed rape); and subspecies, cultivars, varieties and hybrids thereof.

The genus *Sinapis* in the family Brassicaceae includes species, such as *Sinapis hirta* and *Sinapis alba*, and subspecies, cultivars, varieties and hybrids thereof.

In a preferable embodiment the plant of *Brassica* species is *Brassica carinata*.

The seeds of the plant of *Brassica* species may be treated with a doping composition at any point of time, prior to culturing the seeds.

The *Brassica* seeds (seeds of the plant of the *Brassica* species) are doped with a doping composition comprising at least one N-fixing bacteria. The N-fixing bacteria in the doped seeds infects the *Brassica* plant by causing intracellular infection via root hairs, when the seed is planted and propagated, resulting in root colonization. Artificial symbioses between the N-fixing bacteria and the *Brassica* plant are created, whereby the demand of chemical N-fertilizers is greatly reduced.

The *Brassica* seeds may optionally be subjected to one or more of drying, methods to terminate dormancy, methods to speed up germination, seed dressing, pelleting and coating prior to, simultaneously or after treating with the doping composition.

In a preferable embodiment, the *Brassica* seeds are dried prior to treating with the doping composition. Any suitable drying apparatus known in the art may be used. Preferably said seed are dried to obtain moisture (water) content in the seeds of not more than 8 wt %.

Doping Composition

The doping composition comprises at least one nitrogen fixing bacteria.

The N-fixing bacteria is selected from diazotrophic rhizobacteria, *Rhizobium* (including *Rhizobia, Bradyrhizobia, Azorhizobia,* and *Sinorhizobia, Frankia* sp. members of the actinomycete family, nitrogen fixing cyanobacteria (*Nostoc* sp., *Anabaena*), *Acetobacter, Azotobacter, Burkholderia, Enterobacter, Glucenobacter, Gluconacetobacter, Pseudomonas, Beijerinckia, Clostridium, Klebsiella, Spirillum, Azospirillum* spp., *Azoarcus* spp., *Bacillus, Terribacillus* and *Herbaspirillum, Achromobacter, Alcaligenes, Arthrobacter, Azomonas, Corynebacterium, Derxia, Enterobacter, Rhodospirillum, Rhodopseudomonas* and *Xanthobacter*, and combinations thereof.

In an embodiment, the N-fixing bacteria is *Gluconacetobacter diazotrophicus* or, *Gluconacetobacter johannae*.

The nitrogen fixing bacteria may be in dried form, such as in freeze-dried form, which can be reconstituted by water.

In an embodiment the nitrogen bacteria may be microencapsulated.

In an embodiment, the nitrogen fixing bacteria may be the only ingredient or the only active ingredient in the doping composition.

The doping composition may additionally comprise at least one agent capable of inducing nod-factor production in the bacteria. Nod factors enhance nodulation, root hair curling and N-fixing. The agent capable of inducing nod-factor may be selected from flavonoids, plant growth regulators, nutrients and combinations thereof.

The flavonoids may be selected from quercetin, kaempherol, phenol, betaine and hydroxycinnamic acid.

The plant growth regulator, e.g. phytohormone, may be selected from auxins, gibberellins and cytokinins.

Furthermore, the plant growth regulator may act as a germination agent or germinant. Seed germination is the process by which an organism grows from a seed. A dormant seed is unable to germinate in a specified period of time under a combination of environmental factors that are normally suitable for the germination of the non-dormant seed.

Germination phase involves breaking of seed dormancy and subsequent germination. Naturally occurring hormones such as auxins (e.g. indole-3-acetic acid), gibberellins and cytokinins function as germination agents.

The nutrient needed for growth of bacteria, may be selected from vitamins, macrominerals, micronutrients, organic acids, trace minerals and sugars, such as sucrose and 2-O-methyl-D-mannose. When sucrose is used as a nutrient, the amount of sucrose in the doping composition is suitably from 1 to 15% in the medium, such as from 2 to 10%.

The doping composition may additionally comprise at least one agriculturally acceptable excipient or additive known in the art, such as thickening agents, binders, dispersants, surfactants, polysaccharides, diluents, humectants, and carriers.

The polysaccharide may be selected from hydrocolloid polysaccharides derived from animal, plant and microbial sources, such as exudate gum polysaccharides, cellulosic derivatives, starches, polysaccharides derived from seaweed, seed gums, polysaccharides derived from microbial fermentation and nitrogen containing polysaccharides.

The amount of polysaccharide present in the doping composition may vary depending upon factors such as the manner of administration, the type of plant or seed, which is treated, the particular strain of bacteria used, and the level of enhanced nitrogen-fixation required.

The amount of the polysaccharide in the doping composition is suitably from 0.1 to 1% w/w, for example from 0.1 to 0.5% w/w.

In an embodiment, polysaccharide is an exudate gum polysaccharide, for instance gum Arabic, and is included in the doping composition at a concentration of from 0.1 to 1% w/w.

The carrier is an agriculturally acceptable carrier, which is used to deliver active agents (e.g. microorganisms, germinants, agriculturally beneficial ingredients, biologically active ingredients etc) to a seed or seeds. The carriers include liquids, slurries, solids, also wettable powders and dry powders.

In an embodiment, one or more of surfactants, such as emulsifiers, antifoaming agents, and dispersants, are used. The surfactant may be nonionic, anionic, cationic or zwitterionic. In an embodiment a surfactant is an agriculturally acceptable surfactant, suitably a non-ionic surfactant.

The amount of surfactant may vary depending upon the various factors such as the particular surfactant used, the type of seed being treated, the manner of administration, the type of plant or seed to be treated and the particular bacteria strain being used, and the level of enhanced nitrogen-fixation required. The doping composition may comprise from 0.0005 to 10% v/v, such as from 0.0005 to 1% v/v, such as from 0.0005 to 0.5% v/v, for example from 0.0005 to 0.2% v/v, of at least one a surfactant.

The doping composition may additionally comprise at least one biologically active agent known in the art, such as agriculturally active component, insecticide, herbicide or fungicide.

The doping composition may further comprise at least one additional symbiotic bacteria.

In an embodiment, the symbiotic bacteria are selected from *Terribacillus* spp., *Rhizobium* spp., *Bradyrhizobium* spp., *Pseudomonas* spp. and/or *Bacillus* spp., which symbiotic bacteria is different from the N-fixing bacteria. The symbiotic bacteria may be included in the doping composition with N-fixing bacteria either separately or in admixture.

In an embodiment, the combination of at least one N-fixing bacteria and at least one symbiotic bacteria are administered to a seed in a doping composition. The combination of N-fixing bacteria and symbiotic bacteria may be in the form of co-culture, for example in dried form, such as freeze-dried form. The co-culture may be microencapsulated to enhance stability.

The relative amounts of symbiotic bacteria to nitrogen fixing bacteria varies depending for instance upon bacterial growth and the specific strain of nitrogen-fixing bacteria. Preferably, the nitrogen-fixing bacteria remains the predominant bacteria strain present. The amount of the symbiotic bacteria may be from 0.1 to 50% of the total bacteria, such as from 1 to 45%, for example from 1 to 30%, such as from 1 to 20% of the total bacteria. The doping composition may additionally comprise at least one symbiotic fungus.

In an embodiment, the symbiotic fungus is selected from *Trichoderma* spp., *Piriformospora* sp., *Penicillium* spp., *Fusarium* spp. and/or *Rhizoctonia* spp. A symbiotic fungus may be included in the doping composition with N-fixing bacteria either separately or in admixture, optionally in microcapsulated form.

In an embodiment symbiotic fungus and symbiotic bacteria may be used in combination in the doping composition.

The doping composition may be in the form of liquid, solution, emulsion, oil solution, suspension, foam, spray, aerosol, dust, gel, paste, or in the form of a solid composition such as granule or capsule, powder, such as wettable powder or soluble powder, or any other suitable format. The doping composition may be used in diluted form or as a concentrate. Solid composition such as capsule, granule or powder is dissolved in liquid, e.g. water, before using it for coating of the seeds.

The amount of the N-fixing bacteria in the doping composition is adjusted depending upon the strain of nitrogen-fixing bacteria, the type of seed being treated, the method of administration and the level of an optional germination agent.

In an embodiment, the doping composition comprises from 1 to $1 \times 10^9$ bacteria per milliliter of doping composition.

In an embodiment, the doping composition comprises from 1 to $1 \times 10^8$ nitrogen fixing bacteria per milliliter of doping composition.

In an embodiment, the doping composition comprises from 1 to $1 \times 10^7$ nitrogen fixing bacteria per milliliter of doping composition.

In an embodiment, the doping composition comprises from 1 to $1\times10^6$ nitrogen fixing bacteria per milliliter of doping composition.

In an embodiment, the doping composition comprises from 1 to $1\times10^5$ nitrogen fixing bacteria per milliliter of doping composition.

In an embodiment, the doping composition comprises from 1 to $1\times10^4$ nitrogen fixing bacteria per milliliter of doping composition.

In an embodiment, the doping composition comprises from 10 to $10^3$ nitrogen fixing bacteria per milliliter of doping composition.

In an embodiment, the doping composition comprises from 50 to 200 nitrogen fixing bacteria per milliliter of doping composition.

In an embodiment, the doping composition comprises from 1 to 100 nitrogen fixing bacteria per milliliter of doping composition.

The bacteria are cultured and detected using any conventional method known in the art.

In an embodiment, the bacteria are cultured to a readily detectable level for example by examining the optical density and diluting the solution accordingly.

In an embodiment, the doping composition comprises a solvent selected from water, organic solvents, and mixtures thereof. Preferably the organic solvent, such as vegetable oil or hydrocarbon such as paraffin oil or kerosene oil may be used. Suitable vegetable oils are such as soybean oil, sunflower oil, canola oil (oilseed rape oil), cottonseed oil, castor oil, linseed oil or palm oil and mixtures of these.

In an embodiment the doping composition comprises N-fixing bacteria and water.

In an embodiment the doping composition comprises N-fixing bacteria, water and sucrose.

In an embodiment the doping composition comprises N-fixing bacteria, water, sucrose and a non-ionic surfactant (such as Tween®).

In an embodiment the doping composition comprises N-fixing bacteria, water, sucrose, gum Arabic and non-ionic surfactant.

In an embodiment the doping composition comprises N-fixing bacteria, water and gum Arabic.

In an embodiment the doping composition comprises N-fixing bacteria, water, sucrose and gum Arabic.

Doping of *Brassica* Seeds (Doping Step)

Any conventional application method known in the art may be used to apply the doping composition to the *Brassica* seeds.

The doping can be carried out using any methods ranging from conventional dressing to coating and pelleting. In all cases, the product is delivered to the seed at the correct dose and as uniformly as possible from seed to seed. The seed may be dressed in a dry formulation or wet treated with a slurry or liquid formulation. In seed coating method, typically a binder is used with a formulation to enhance adherence to the seed and having impact on seed size and shape. Seed pelleting technology results in changing the physical shape of a seed, particularly to enhance plantability and handling. For example, bacteria and other components of the doping composition may be formulated to prepare a composition, such as a liquid suspension, wherein the seeds are doped or immersed. An aqueous doping composition may be sprayed on the seeds.

In an embodiment, seeds are treated using pelleting or film-coating with conventional processes known in the art.

In an embodiment, the seeds of a plant selected from *Brassica* species are doped with a doping composition comprising at least one N-fixing bacteria in a doping step. The doping step may be performed once or several times.

The seeds may be dried after the doping step to form a residual coating comprising N-fixing bacteria.

The seeds may be treated at seeding, or immediately prior to seeding, for instance within hours of sowing seeds. Alternatively, seeds may be treated days, weeks, or months before seeding.

The doped seeds, i.e. the seeds treated with the doping composition are planted using any agricultural machinery, such as planter or sowing machine. Seeds may be planted with or without tillage.

*Brassica* seed crop may be harvested using any agricultural machinery used for oil seed crops.

The *Brassica* seed crop may be stored in suitable storage vessels, such as in vertical cell-like storage bins. Proper handling and storage of oil-containing materials help minimizing problems such as deterioration and sprouting, as well as maintain good quality of both contained oil and meal.

Preconditioning of *Brassica* Seed Crop

The harvested *Brassica* seeds may be subjected to at least one preconditioning step, such as cleaning, drying, dehulling, size reduction, flaking cooking and tempering, etc. prior to the treating step.

The seeds may be cleaned to remove plant stems, sticks, leaves and foreign material before storage. Foreign materials in seeds are typically separated out by a combination of rotating or vibrating coarse screens, reels and aspiration.

The moisture content of seeds may be reduced to minimize degradation in storage and to improve the effectiveness of downstream processing, using any suitable grain driers.

Typically, seeds need to be separated from their outer husk or shell prior to oil pressing and extraction. Conventional dehullers, such as knife, disk and impact type dehullers may be used.

The seeds may also be subjected to heating to about 30-40° C. Heating helps to improve the screw-pressing capacity, cake formation, extractability, and solvent recovery from the extracted oilseeds.

The seeds may be reduced in size or flaked. Flaking of oilseeds increases surface area for increased contact between solvent and seed particularly during the solvent extraction process.

The seeds may be cooked or tempered to denature proteins, release oil from the cells and inactivate enzymes. The heating may be carried out with steam, either by direct or indirect heating. Typically, the cooked seeds may be immediately pressed to separate oil. Cooking improves seed elasticity for efficient pressing.

Treating of *Brassica* Seed Crop (Treating Step)

The *Brassica* seed crop, which is optionally subjected to preconditioning, is treated to obtain *Brassica* seed oil, using suitable treating methods. Said methods may be selected from pressing and extraction methods and combinations thereof.

In an embodiment, the *Brassica* seed crop is subjected to at least one of pressing and solvent extraction obtain *Brassica* seed oil and meal.

In an embodiment, seeds or seed flakes are pressed to provide seed oil. Suitably the pressing may be carried out in screw presses. The objective of pressing is to remove as much oil as possible.

Since, in many cases, pressing alone cannot remove all the oil from the seeds, the press cake may be solvent extracted to remove the remaining oil. The cake from the pressing (press cake), containing oil, may be subjected to solvent extraction in which an organic solvent (such as n-alkane) is used. Basket and continuous loop type extractors are examples of suitable extractors.

The solvent may be removed from the marc (solvent saturated meal) in a desolventizer-toaster. The majority of the solvent may be flashed from the meal by heating it on heat surfaces. Final stripping of the solvent may suitably be completed by injecting live steam through the meal, a process termed toasting. The meal is then cooled and dried.

Converting of Feedstock Comprising *Brassica* Seed Oil (Conversion Step)

Feedstock comprising *Brassica* seed oil is converted in a conversion step, whereby renewable fuel or fuel components are obtained. The conversion step may be carried out as catalytic hydroprocessing in the presence of hydrogen, or as catalytic deoxygenation, or transesterification, to yield at least one effluent from the conversion. The product obtained from the conversion step may be subjected to fractionation and/or further processing stages for providing liquid fuels and other chemicals. The product may comprise hydrocarbons or fatty acid esters, suitable as renewable fuels or renewable fuel components.

The feedstock comprising *Brassica* seed oil may additionally comprise seed oil obtained from seed crop harvested from *Brassica* species or oil seed plant species farmed in the farming season preceding or succeeding the first farming season.

The conversion step may optionally comprise pretreating of feedstock comprising *Brassica* seed oil, where said feedstock (oil) is refined or purified.

In an embodiment the conversion step comprises pretreating of feedstock comprising *Brassica* seed oil, followed by subjecting it to conversion selected from catalytic hydroprocessing, catalytic deoxygenation and transesterification.

Feedstock comprising *Brassica* seed oil (which is optionally pretreated) is converted whereby renewable fuel or renewable fuel components are obtained. The converting may be carried out as catalytic hydroprocessing in the presence of hydrogen, or as catalytic deoxygenation, or as transesterification, to yield at least one effluent (product) from the conversion. The effluent(s) may comprise hydrocarbons or fatty acid esters, suitable as renewable fuels or renewable fuel components.

The effluent(s) may be subjected to fractionation and/or further processing steps for providing liquid fuels and other chemicals.

Optionally, in addition to *Brassica* seed oil, one or more of bio oils derived from biomass, e.g. bio oils obtained by pyrolysis, hydropyrolysis or by supercritical treatment, other plant derived bio oils, animal fat(s), tallow, acid oils, used bio oils that have optionally been treated separately, mineral oil feedstocks or fractions originating from mineral oil or coal, and any combinations thereof may be fed to the conversion step.

Said conversion may be carried out in one step, or in more than one steps.

In an embodiment, the conversion is carried out in gas phase. In another embodiment, the catalytic conversion is carried out in liquid phase.

Catalytic Hydroprocessing

In an embodiment, the feedstock comprising *Brassica* seed oil (typically comprising C4-C26 free fatty acids and/or acylglycerols), optionally pretreated, is subjected to a catalytic hydroprocessing step. The obtained least one effluent (hydroprocessing product) may be fractionated in a fractionating step to provide hydrocarbon fractions, suitable as renewable fuels or fuel components, useful as transportation fuels, fuel components and other chemicals.

Optionally, in addition to *Brassica* seed oil, one or more of bio oils derived from biomass, e.g. bio oils obtained by pyrolysis, hydropyrolysis or by supercritical treatment, other plant derived bio oils, animal fat(s), tallow, acid oils, used bio oils that have optionally been treated separately, or mineral oil feedstocks or fractions originating from mineral oil or coal, may be fed to the hydroprocessing step.

Said catalytic hydroprocessing step may be carried out in one step, or in more than one steps. The feedstock(s) may be heated, if necessary, before feeding to the hydroprocessing.

In an embodiment, the catalytic hydroprocessing is carried out with a catalyst effecting one or more of removing oxygen and other heteroatoms, effecting isomerization, effecting dearomatization, effecting cracking, effecting hydroisomerization, effecting hydrocracking, or a combination of said catalysts.

The catalytic hydroprocessing comprises at least a hydrodeoxygenation step. Catalytic hydroprocessing may also comprise a hydrodeoxygenation step followed by one or more steps selected from isomerization, hydrodewaxing, hydrodearomatization and hydrocracking steps.

The hydrodeoxygenation (HDO) is performed by using one or more catalysts capable of removing oxygen and other heteroatoms, such as sulfur and nitrogen from organic compounds as well as catalysing hydrogenation of unsaturated bonds. The catalysts may comprise one or more metals selected from Group 6 and Groups 8, 9 and 10 (IUPAC 2016) metals. Particularly useful examples are Mo, W, Co, Ni, Pt and Pd. Also, mixtures of these, i.e. CoMo, NiMo and NiW are effective and may be used. The catalyst(s) may also contain one or more support materials, for example zeolite, alumina ($Al_2O_3$), gamma-alumina, zeolite-alumina, alumina-silica ($SiO2$), $ZrO2$, alumina-silica-zeolite and activated carbon. $NiMo/Al_2O_3$, $NiMo/SiO_2$, $CoMo/Al_2O_3$, $CoMo/SiO_2$ or NiW/zeolite-alumina, or Pt and/or Pd on gamma-alumina may be used as HDO catalysts. If a catalyst comprising NiMo, CoMo and/or NiW is used, the catalyst is in sulphided state.

In an embodiment, a solid catalyst comprising $NiMo/Al_2O_3$ or $NiMo/SiO_2$ is used as HDO catalyst.

In another embodiment, a solid catalyst comprising $CoMo/Al_2O_3$ or $CoMo/SiO_2$ is used.

Another effective hydrodeoxygenation catalyst is a multifunctional catalyst capable of catalysing the same reactions as HDO catalysts. In addition, multifunctional catalysts can effect isomerization, dearomatization and cracking. Both isomerization and cracking can improve cold flow properties. These catalysts can also be called hydrodewaxing (HDW) catalysts. Useful HDW catalysts are aluminosilicate molecular sieves, i.e. zeolites such as ZSM-5, ZSM-11, ZSM-12, ZSM-22, ZSM-23, ZSM-35, zeolite beta and zeolite Y. Also, NiW supported on alumina, zeolite-alumina or alumina-silica-zeolite may be used.

In one embodiment, NiW on a zeolite-alumina support is used as a multifunctional catalyst. NiW has excellent isomerizing, cracking and dearomatization properties and it also has the capacity of performing the hydrodeoxygenation, hydrodesulfurization and other hydrogenation reactions of biological feed materials.

In another embodiment, NiW on alumina-silica-zeolite support is used as a multifunctional catalyst.

The temperature of the hydrodeoxygenation is 250-400° C., preferably 280-360° C. and most preferably 280-350° C. The pressure (abs) of the hydrodeoxygenation is 20-160 bar, preferably 40-10 bar, particularly preferably 45-100 bar. The WHSV (weight hourly space velocity) varies between 0.1 and 10, preferably between 0.2 and 5.

The catalytic hydroprocessing may also comprise a hydrodewaxing step to induce selective hydroisomerization and hydrocracking of n-paraffins. A catalyst comprising a multifunctional catalyst, as described above, may be used as a hydrodewaxing (HDW) catalyst. Also, a molecular sieve, in combination with at least one metal of the Group 8, 9 or 10 may be used as hydrodewaxing catalyst. The molecular sieve may comprise zeolites (e.g. mordenite, ZSM-5, ZSM-12, ZSM-22, ZSM-23, SSZ-32, ZSM-35, ZSM-48, EU-2 and MCM-68) or silica-alumina phosphate materials (e.g. SAPO-11). ZSM-5 may optionally be used in its HZSM-5 form, in the absence of any metal of Groups 8, 9 or 10. Suitable metals of Groups 8, 9 or 10 are nickel, cobalt, platinum and palladium. Examples of possible combinations are Pt/ZSM-35, Ni/ZSM-5, Pt/ZSM-23, Pd/ZSM-23, Pt/ZSM-48, Pt/EU-2 and Pt/SAPO-11. The hydrodewaxing catalyst may also comprise a binder, such as silica, alumina, silica-alumina, zirconia, magnesia or a mixture of these. The catalyst may be a silica bound dealuminated (AHS treated) Pt/ZSM-12 catalyst. Also, NiW on zeolite-alumina support may be used as HDW catalyst.

The temperature of the hydrodewaxing step is 200-450° C., preferably 280-400° C., particularly preferably 290-400° C. The pressure is 20-160 bar, preferably 40-100 bar, particularly preferably 45-95 bar. The WHSV varies between 0.1 and 6, preferably between 0.3 and 5.

Catalytic hydroprocessing may also comprise an hydroisomerisation step, where hydroisomerization (HI) catalysts may be used. The HI catalysts are capable of branching of the hydrocarbon chain, thus improving the cold flow properties of the product. Hydroisomerization catalysts are also capable of inducing at least some cracking reactions. Suitable catalysts contain at least one metal of Groups 8, 9 or 10 (e.g. Pt, Pd, Ni) and/or a molecular sieve. Preferred molecular sieves are zeolites (e.g. ZSM-22 and ZSM-23) and silicoaluminophosphates (e.g. SAPO-11 and SAPO-41). HI catalysts may also contain one or more of the support and/or binder materials described above. In one embodiment, the HI catalyst comprises Pt, a zeolite and/or silicoaluminophosphate molecular sieve, and alumina. The support may alternatively or additionally contain silica. Also, amorphous alumina and amorphous silica-alumina may be used as support materials. Typical isomerization catalysts are, for example, Pt/SAPO-11/$Al_2O_3$, Pt/ZSM-22/$Al_2O_3$, Pt/ZSM-23/$Al_2O_3$, Pt/SAPO-11/$SiO2$. Also, NiW on zeolite-alumina support may be used as HI catalyst.

The temperature of the hydroisomerization step is 200-450° C., preferably 280-400° C., particularly preferably 300-400° C. The pressure is 20-160 bar, preferably 40-100 bar, particularly preferably 45-95 bar. The WHSV varies between 0.1 and 6, preferably between 0.3 and 5.

The catalytic hydroprocessing may also comprise a hydrodearomatization step where hydrodearomatization (HDA) catalysts may be used. HDA catalysts are capable of breaking the aromatic ring structures of the aromatic hydrocarbons.

The HDA catalyst is selected from catalysts containing one or more metals of the Groups 8, 9 or 10 of the IUPAC Periodic table of Elements (2016), Group 6 and the rare earth metals. Suitably the metal is selected from Pt, Pd, Ir, Ru, Rh, Re, Ni, Co, Mo or W, in elemental, oxide or sulphide form, and mixtures and combinations thereof.

Suitably said catalyst comprises a support selected from oxide supports, such as alumina, titania, silica, magnesia, zirconia, and $B_2O_3$, and other supports, such as carbon, charcoal, zeolites, and combinations thereof, suitably $Al_2O_3$, $Al_2O_3$—$SiO_2$, zeolite Y, $Al_2O_3$—$B_2O_3$, $SiO_2$ or combination thereof. The catalyst may be promoted (or acid promoted) for increasing the acidity of the support whereby sulphur tolerance of the catalyst is improved. Examples of suitable sulfur tolerant catalysts are metal sulfides, Pd and/or Pt on zeolite Y/$Al_2O_3$, optionally with added Na; Pd and/or Pt on zirconia/silica, optionally with added alumina or alumina-silica; Pd and/or Pt on alumina/alumina-silica, optionally with one or more of titania, silica, magnesia, zirconia; Pd or Pt or Ir on carbon, or charcoal, suitably Pd promoted with tantalum perfluoride and hydrogen fluoride; Pd, Pt, Ir, Ru, Rh; Re on silca/alumina, sulphidized CoMo and NiMo catalysts on alumina/alumina-silica; and Pd—Pt on $Al_2O_3$—$B_2O_3$. By using suitably modified supports, the HDA catalysts containing noble metals such as Pd, Pt, Ir, Ru, Rh and/or Re, can maintain their activity even in sulfur containing process conditions.

The temperature of the hydrodearomatization step is 85-450° C., suitably 200-450° C., preferably 280-400° C., particularly preferably 300-400° C. The pressure of the hydrodearomatization step is 20-160 bar, preferably 40-100 bar, particularly preferably 45-95 bar. The WHSV varies between 0.1 and 6, preferably between 0.3 and 5.

In an embodiment, hydroaromatization is carried out using a catalyst comprising elemental Ni on a support, at the temperature of 85-160° C. and under a pressure of 20-40 bar.

As an example, NiW on a support selected from the group consisting of Al2O3, zeolite, zeolite-$Al_2O_3$, $Al_2O_3$—$SiO_2$ and activated carbon may be used as HDA catalyst. In an embodiment, NiW on alumina-silica-zeolite support is used as a HDA catalyst. In another embodiment, Pt on zeolite Y/$Al_2O_3$ is used as a HDA catalyst.

The catalytic hydroprocessing may also comprise a hydrocracking step, where hydrocracking (HC) catalysts may be used. HC catalysts decrease the hydrocarbon chain length and convert high boiling point, high molecular weight hydrocarbons into lower boiling range, lower molecular weight compounds. HC catalysts are active in cracking of carbon-carbon bonds as well as hydrogenation of unsaturated molecules in the feedstock.

The HC catalysts are selected from catalysts containing one or more metals of the Groups 8, 9 or 10 and/or Group 6 metals, on a suitable support. Acidic supports, such as zeolites, may be used either alone or mixed with a carrier matrix. Suitable catalysts are Pd or Pt containing catalysts or sulfided catalysts comprising Mo or W in combination with Ni or Co. Suitable catalysts include NiMo supported on gamma alumina or on ZSM-5, Pt supported on Y zeolite or on ZSM-5 or NiW on zeolite-alumina. The HC catalyst may also comprise a suitable binder, for example inorganic oxide material, such as alumina. In an embodiment, NiW on zeolite-alumina is used as HC catalyst.

The temperature of the hydrocracking step is 200-480° C., preferably 250-450° C., particularly preferably 280-450° C. The pressure of the hydrocracking step is 20-160 bar, preferably 40-100 bar, particularly preferably 45-95 bar. The WHSV varies between 0.1 and 15, preferably between 0.3 and 5.

The different steps of the catalytic hydroprocessing may be arranged in several ways, according to the feedstock and taking into account the desired product to be produced.

The hydroprocessing step may be performed using a step a) as the first step, followed by one or both of the following steps b) and c), and optionally step d) and/or e), where steps a)-e) are denoted as:
 (a) hydrodeoxygenation step,
 (b) hydroisomerization step,
 (c) hydrodewaxing step, (d) hydrodearomatization step,
(e) hydrocracking step.

Suitable hydroprocessing step configurations are:
(a) and (b);
(a) and (c);
(a), (b) and (c);
(a), (b) and (d);
(a), (c) and (d); and
(a), (b), (c) and (d).

In one embodiment, the catalytic hydroprocessing comprises a hydrodeoxygenation step (a), followed by a hydroisomerization step (b), and/or hydrodewaxing step (c), and/or a hydrodearomatization step (d).

In another embodiment, the catalytic hydroprocessing comprises a hydrodeoxygenation step (a), followed by a hydroisomerization step (b), hydrodewaxing step (c) and a hydrodearomatization step (d).

Yet in another embodiment, the catalytic hydroprocessing comprises a hydrodeoxygenation step (a), followed by a hydroisomerization (b) step or hydrodewaxing step (c).

Yet in another embodiment, the catalytic hydroprocessing comprises a hydrodeoxygenation step (a), followed by a hydroisomerization (b) step and hydrodewaxing step (c).

Yet in another embodiment, the catalytic hydroprocessing comprises a hydrodeoxygenation step (a), followed by a hydroisomerization (b) step and hydrodearomatization step (d).

Yet in another embodiment, the catalytic hydroprocessing comprises a hydrodeoxygenation step (a), followed by a hydrodewaxing step (c) and hydrodearomatization step (d).

The hydroprocessing may also comprise a hydrocracking step (e) as the last step, resulting in the following configurations:
(a), (b) and (e);
(a), (c) and (e);
(a), (b), (c) and (e);
(a), (b), (d) and (e);
(a), (c), (d) and (e); and
(a), (b), (c), (d) and (e).

In one embodiment, the catalytic hydroprocessing comprises a hydrodeoxygenation step (a), followed by a hydroisomerization step (b), and/or hydrodewaxing step (c), and/or a hydrodearomatization step (d), and or hydrocracking step (e).

In another embodiment, the catalytic hydroprocessing comprises a hydrodeoxygenation step (a), followed by a hydroisomerization step (b), hydrodewaxing step (c) and a hydrocracking step (e).

Yet in another embodiment, the catalytic hydroprocessing comprises a hydrodeoxygenation step (a), followed by a hydroisomerization (b) step and hydrocracking step (e).

Yet in another embodiment, the catalytic hydroprocessing comprises a hydrodeoxygenation step (a), followed by a hydrodewaxing step (c) and hydrocracking step (e).

Yet in another embodiment, the catalytic hydroprocessing comprises a hydrodeoxygenation step (a), followed by a hydroisomerization (b) step, hydrodearomatization step (d) and hydrocracking step (e).

Yet in another embodiment, the catalytic hydroprocessing comprises a hydrodeoxygenation step (a), followed by a hydrodewaxing step (c), hydrodearomatization step (d) and hydrocracking step (e).

Yet in another embodiment, the catalytic hydroprocessing comprises a hydrodeoxygenation step (a), followed by a hydroisomerization (b) step, hydrodewaxing step (c), hydrodearomatization step (d) and hydrocracking step (e).

In an embodiment, the catalytic hydroprocessing comprises a hydrodeoxygenation step (a), where a hydrodeoxygenation product is obtained, followed by treating the hydrodeoxygenation product in a hydroisomerization step (b), and/or in a hydrodewaxing step (c), and/or in a hydrodearomatization step (d), and or in a hydrocracking step (e) to obtain hydroprocessed product.

As can be realized from the description above, both HDW and HDA catalysts are capable of inducing the same reactions, for example breaking aromatic ring structures. HDW catalysts are also capable of inducing isomerization reactions. Thus, it is possible to use a multifunctional HDA/HDW catalyst(s) after step (a) as the catalyst in the following step/steps, before the hydrocracking step (e). The hydroprocessing configuration in such a case is as follows: (a), (c)/(d) and (e), where in steps (c)/(d) a multifunctional HDW/HDA catalyst may be used.

It is also possible to use separate HDW and HDA catalysts, as a combination in a same catalyst bed, by either layering or mixing them. In such an embodiment, both HDW and HDA catalyst are used in a sulfided form.

In one embodiment, in the hydrodeoxygenation step, one or more HDO catalysts may be used.

In another embodiment, only HDW catalysts are used in the hydrodeoxygenation step. In an embodiment, where hydroprocessing comprises a hydrodeoxygenation step followed by a hydroisomerization step, in the hydrodeoxygenation step at least one hydrodeoxygenation (HDO) catalyst and/or at least one hydrodewaxing (HDW) catalyst is used, and in the hydroisomerizing step at least one (HI) catalyst is used. Suitably the catalysts are arranged in such a way that the HDO/HDW catalyst is arranged upstream from the HI catalyst in the flow direction of the feedstock. The HI catalyst is suitably arranged in a separate reactor(s) downstream from the reactor(s) containing HDO/HDW catalyst. Suitably separation of a light gaseous side stream is carried out after the hydrodeoxygenation to remove sulfur compounds from the hydrodeoxygenated product before it is reacted with HI catalyst in the case that HI catalyst contains a sulfur sensitive Group VIII noble metal.

In another embodiment, the hydroprocessing comprises a hydrodeoxygenation step followed by a hydrodewaxing step and/or hydrodearomatising step. In the hydrodeoxygenation step at least one hydrodeoxygenation (HDO) catalyst and/or at least one hydrodewaxing (HDW) catalyst is used and in the hydrodewaxing step and/or hydrodearomatizing step at least one HDW and/or at least one HDA catalyst is used. In another embodiment the hydrodewaxing/hydrodearomatizing step is followed with a hydrocracking step.

The hydrocracking catalyst(s) in the hydrocracking step are preferably loaded in a separate reactor, which may comprise one or more catalyst beds of hydrocracking catalyst(s).

In an embodiment, in the hydrocracking step, hydrocracking of the product of the previous step(s) b) to d) or heavy compounds separated from the product from the previous step(s) b) to d) is carried out.

In an embodiment, the catalytic hydroprocessing step comprises a guard bed step, arranged upstream of the first hydroprocessing bed or reactor.

The hydroprocessing reactions are highly exothermic, whereby the temperature can rise to a level which is detrimental to the stability of the catalyst and/or product quality. Recirculation of the hydrocarbon fractions or products and/or purified effluent gas to the reactor(s) may be used to control the temperatures.

Additionally, the hydrocarbon product and/or purified gases may be directed for quench purposes between one or more catalyst beds.

At least one effluent from the hydroprocessing is drawn off from the last reactor. In one embodiment, the effluent is directed to a separator, such as any suitable separator or flashing unit. In the separator, typically water, gaseous stream comprising hydrogen, light hydrocarbons (such as C1-C5 hydrocarbons), H2S, CO and CO2 are separated from the liquid component comprising >C5 hydrocarbons and some C1-C5 hydrocarbons. Water and gases may also be separated by other means which are well known to those skilled in the art.

The obtained liquid component (hydroprocessing product) is suitably fractionated in a fractionating step to provide hydrocarbon fractions usable as liquid transportation fuels, fuel components and other chemicals.

Catalytic Deoxygenation

In an alternative embodiment, the conversion step may be carried out as catalytic deoxygenation.

In an embodiment, a metal catalyst, such as a catalyst comprising Ni, Ni/Mo, Ru, Pt, Pd, Ir, Os or Re is used in the deoxygenation.

In an embodiment, the catalytic deoxygenation is carried out at the temperature of 270-400° C.

In an embodiment, the catalytic deoxygenation is carried out at 4-8 bar.

The catalytic deoxygenation may be carried out in the presence of hydrogen, or alternatively without hydrogen.

Transesterification

In an alternative embodiment, the conversion step may be carried out as transesterification.

Transesterification of *Brassica* seed oil comprising acylglycerols is carried out with an alcohol in the presence of a catalyst or without a catalyst, using methods well known in the art. The alcohol is suitably C1-C5 alcohol, preferably methanol or ethanol is used. The transesterification method may comprise one or more step. In the case a catalyst is used, said catalyst may be a homogeneous or heterogeneous catalyst, which is an alkaline or acidic catalyst, also bifunctional catalysts may be used. The formed fatty acid esters are retrieved as product.

The temperature in the transesterification is suitably from 50 to 300° C. The transesterification is suitably carried out under pressures from 1 to 100 bar.

The process conditions in the transesterification are selected depending on selected method.

Pretreating of Feedstock Comprising *Brassica* Seed Oil

The feedstock comprising *Brassica* seed oil may optionally be pretreated before feeding it to any of catalytic hydroprocessing, catalytic deoxygenation or transesterification. The pretreatment may comprise at least one of physical and chemical pretreatment methods of seed oil, where said pretreating may comprise at least one of degumming, bleaching, hydrolysis, soap stock splitting, deacidification, alkali neutralization, cold neutralization, micella refining, deodorization, and combinations thereof.

In one embodiment, the feedstock comprising *Brassica* seed oil is treated with methanol in the presence of sodium hydroxide catalyst.

In an embodiment, the feedstock comprising *Brassica* seed oil is degummed.

Degumming methods, such as water degumming, acid degumming, deep degumming utilizing agents able to chelate particularly Fe, Ca and Mg, enzymatic degumming, and alkali refining may be used for removal of gum from *Brassica* seed oil. Water degumming consists of treating heated natural oil with water, followed by centrifugal separation, whereby phospholipids are separated as degumming residue (waxy or gummy solids). Hydrating the gums and removing the hydrated gums from the *Brassica* seed oil before subjecting the oil to catalytic conversion prevents catalyst poisoning.

Residue resulting from the degumming may be spread to the field as a fertilizer. Optionally, the degumming residue is composted prior to recycling to the soil as a fertilizer. In both cases phosphorus and nitrogen are recovered. Composting enables making nitrogen and phosphorous easily available to the plants and reduces the need for additional nitrogen and phosphorus fertilizers.

In an embodiment, *Brassica* seed oil is bleached.

In an embodiment, *Brassica* seed oil is degummed and bleached, where the bleaching is carried out after degumming of the seed oil.

The bleaching process may suitably be applied after degumming and it is more appropriately referred to as adsorption treatment. Seed oil may still contain undesirable substances such as phosphatides and metals at trace concentrations. These impurities from crude oils may be removed by using materials with a strong adsorption power. Said materials include bleaching earths, such as bentonites and other clay adsorbents. In the bleaching the clay adsorbents are mixed with the oil to remove unwanted contaminants.

The feedstock comprising *Brassica* seed oil, obtained from pretreating, may be converted to renewable fuel or renewable fuel components.

In the conversion step, at least one effluent (product from the conversion step) is obtained. The effluent is directed to a separator, where a liquid stream comprising hydrocarbons having a carbon number of more than 5, or alternatively comprising fatty acid esters having carbon number of more than in the fatty acid chain and the ester being C1-C5 ester, is suitably drawn off from the outlet from a separator and subjected to fractionation. The liquid stream may be fractionated to hydrocarbon fractions or fatty acid ester fractions using any suitable fractionation methods, such as fractional distillation to obtain hydrocarbon fractions or fatty acid ester fractions. Suitably the liquid stream is fed to a separation column where different fuel grade hydrocarbon fractions or fatty acid ester fractions, i.e. renewable fuels and fuel components are recovered.

Said hydrocarbon fractions or fatty acid ester fractions are useful as renewable fuels and renewable fuel components, particularly as transportation fuels, blending components for fuels, solvents, kerosene, and industrial chemicals.

In an embodiment, the obtained renewable fuels and fuel components comprise fuel grade hydrocarbons or fuel grade fatty acid esters having a boiling point of at most 380° C. according to ISO EN 3405.

In another embodiment, the obtained renewable fuels and fuel components comprise fuel grade fatty acid esters meeting the requirements standardized for fuels, such as EN 14214 for FAME (fatty acid methyl esters).

In an embodiment, a hydrocarbon fraction having a boiling point in the diesel range, i. e. a middle distillate fraction may be obtained, having a typical boiling point from 160° C. to 380° C., meeting characteristics of the specification of EN 590 diesel, is obtained. Also, hydrocarbon fractions distilling at temperatures ranging from 40° C. to 210° C. and at a temperature of about 370° C. can be obtained. These fractions are useful as high-quality gasoline fuel and/or naphtha fuel, or as blending components for these fuels. Additionally, fractions suitable as solvents, aviation fuels, kerosene, industrial chemicals etc. may be obtained.

The person skilled in the art is able to vary the distilling conditions and to change the temperature cut point as desired to obtain any suitable fraction, boiling suitably in the transportation fuel ranges.

EXAMPLES

The following examples are illustrative embodiments of the present invention, as described above, and they are not meant to limit the invention in any way. The invention is illustrated also with reference to the figures.

Example 1

Growing of Seed Crop

Culture of *Gluconacetobacter diazotrophicus* is incubated for 24 hours in a media. A suspension of *G. diazotrophicus* is prepared having $1 \times 10^5$ bacteria/ml and thereafter diluted to water to prepare a doping composition containing $1 \times 10^5$ *G. diazotrophicus* bacteria/ml. *Brassica carinata* seeds are doped by applying on the seeds doping composition comprising $1 \times 10^5$ *G. diazotrophicus* bacteria/ml, water, 3 wt % sucrose, 0.1 wt % Tween and 0.3 wt % of Gum Arabic, followed by drying, to obtain doped *Brassica* seeds. In a summer farming season, wheat seeds are planted, grown and wheat crop is harvested, and wheat residues and roots are left in the field. No tillage is used.

In a first farming (winter) season following the summer farming season, the doped *Brassica carinata* seeds are planted in the soil where the wheat was grown. No tillage is used. Nitrogen fertilizer dosage was 45% of the theoretical maximum nitrogen response for the crop. The *Brassica carinata* crop reaches maturity and it is harvested. Harvesting is conducted with oil-seed harvesters. During crop growing period, *Brassica carinata* seed crop is harvested and plant residues and roots are left in the soil.

Example 2

Preconditioning and Treating *Brassica carinata* Seeds to Seed Oil

*Brassica carinata* seed crop harvested in Example 1 is subjected to seed cleaning, where, during the cleaning, unwanted weeds, seeds, and other material are removed. No agents are added to the seeds for cleaning.

The obtained cleaned *Brassica carinata* seeds are preheated to a temperature of about 30-40° C. to prevent shattering during the flaking process.

The cleaned and preheated *Brassica carinata* seeds are flaked by roller mills to physically rupture the seeds to obtain flaked seeds.

The flaked *Brassica carinata* seeds are subjected to cooking. At the start of cooking, the temperature is rapidly increased which serves to inactivate the myrosinase enzyme present in the seeds. The cooking lasts for about 15-20 minutes and the temperature is about 100°, whereby cooked seed flakes are obtained.

The cooked *Brassica carinata* seed flakes are pressed in screw presses to obtain *Brassica* seed oil and *Brassica* press cake. The objective of pressing is to remove as much oil as possible, usually about 50 wt % of the seed oil content.

The *Brassica* press cake from the screw press, containing oil, is subjected to solvent extraction (n-hexane) to remove the remaining oil. The marc (hexane-saturated meal) that leaves the solvent extractor, after a fresh solvent wash, typically contains less than 1% oil.

The *Brassica* seed oil obtained in pressing and solvent-extraction is combined for use in the converting.

Hexane is removed from the marc in a desolventizer-toaster. The majority of the solvent is flashed from the marc by heating it on heat surfaces, followed by stripping of the solvent (toasting). During the desolventing-toasting the marc is heated to about 100° C. and moisture increases to about 20 wt %. The marc is then cooled and dried to result meal.

Example 3

Pretreating of *Brassica carinata* Seed Oil

*Brassica carinata* seed oil (obtained from example 2) is pretreated by utilizing degumming and bleaching, whereby said seed oil is purified.

In degumming hot water is added to *Brassica carinata* seed oil since impurities like phospholipids, gums and proteins are soluble in oil but insoluble in water. The impurities (gums) are separated from seed oil by centrifugation. The separated degumming residue (once dry) can be made into lecithin, added into cakes or meal, or composted and recycled as a fertilizer.

The seed oil from water degumming is further subjected to acid degumming at about 80° C. temperature, where citric acid is added, followed by addition of water. Gums are removed as degumming residue from the seed oil by centrifuging. The degummed seed oil is dried, and degumming residues are combined and recycled as a fertilizer.

The degummed seed oil is further bleached with clay adsorbent (bentonite), which is mixed with the oil to remove impurities, such as phosphatides and metals.

*Brassica carinata* seed oil, obtained from degumming and bleaching, is directed to hydroprocessing.

Example 4

Hydroprocessing of *Brassica carinata* Seed Oil

*Brassica carinata* seed oil, obtained in example 3, is fed into a catalytical hydrotreatment process which comprises several catalytical reactors. The operating conditions are set at 20-100 bar and 250-400° C. The reactors are packed with catalysts capable of inducing hydrotreatment, hydrogenation, hydrodeoxygenation (HDO), hydrodearomatization (HDA), hydrodenitrification (HDN) hydrodesulfurization (HDS) and hydrodewaxing (HDW), hydroisomerization (HI) and hydrocracking (HC) reactions. The catalysts comprise sulfided $NiMo/Al_2O_3$ and $NiW/zeolite/Al_2O_3$ catalysts. The effluent obtained from the hydrotreatment is directed to separation and fractionation to obtain renewable fuels or fuel components.

The reduction of the GHG gases, particularly $N_2O$, was 30% compared to the theoretical maximum GHG release of a method where a *Brassica* plant, without doping with any nitrogen fixing bacteria, is cultivated in a rotational manner.

The invention claimed is:

1. A method for producing renewable fuels and renewable fuel components, where the method comprises the steps, where, seeds of *Brassica carinata* are doped with a doping composition comprising at least one nitrogen-fixing bacteria comprising *Gluconacetobacter* to obtain doped *Brassica carinata* seeds, in a first farming season, the doped *Brassica carinata* seeds are planted in soil and a *Brassica carinata* seed crop is harvested, in a farming season preceding or succeeding the first farming season, at least one plant selected from *Brassica carinata*, grain species or forage species is grown in the soil, the *Brassica carinata* crop, grain crop or forage crop obtained in the farming season preceding or succeeding the first farming season is harvested, and at least part of plant biomass is left in and/or on the soil, the *Brassica carinata* seed crop is treated to obtain *Brassica carinata* seed oil and meal, and feedstock comprising the *Brassica carinata* seed oil is converted in a converting step, whereby renewable fuel or renewable fuel components are obtained;

wherein greenhouse gas emission over the course of the method is reduced by over 30% relative to a theoretical maximum greenhouse gas emission of a method wherein a *Brassica carinata* plant, without doping with a nitrogen fixing bacteria, is cultivated in a rotational manner.

2. The method according to claim 1, where in the farming season preceding or succeeding the first farming season, seeds of *Brassica carinata* doped with a doping composition comprising at least one nitrogen-fixing bacteria, or the seeds of *Brassica carinata* are not doped.

3. The method according to claim 1, wherein the converting step comprises pretreating the feedstock comprising the *Brassica carinata* seed oil with a method selected from degumming, bleaching, hydrolysis, soap stock splitting, deacidification, alkali neutralization, cold neutralization, micella refining, deodorization, and combinations thereof.

4. The method according to claim 1, wherein the grain species is selected from the group consisting of wheat, rye, barley, oats, rice, sorghum, maize, millet, vegetables, buckwheat, quinoa, fonio, teff, spelt, edible oil seed plant species, and the forage species is selected from grasses.

5. The method according to claim 1, wherein the doping composition comprises at least one agent capable of inducing nod-factor, and/or wherein the doping composition comprises at least one of germinant, excipient, thickening agent, binder, dispersant, surfactant, polysaccharide, diluent, humectant, carrier and combinations thereof.

6. The method according to claim 1, wherein the converting of the *Brassica carinata* seed oil is carried out by catalytic hydroprocessing, deoxygenation or transesterification.

7. A method for reducing nitrate release in renewable fuel production, where the method comprises the steps, where,
    seeds of *Brassica carinata* are doped with a doping composition comprising at least one nitrogen-fixing bacteria comprising *Gluconacetobacter* to obtain doped *Brassica carinata* seeds,
    in a first farming season, the doped *Brassica carinata* seeds are planted in soil and a *Brassica carinata* seed crop is harvested,
    the *Brassica carinata* seed crop is treated to obtain *Brassica carinata* seed oil and meal, and
    feedstock comprising the *Brassica carinata* seed oil is converted in a converting step, whereby renewable fuel or renewable fuel components are obtained.

8. The method according to claim 7, wherein the method comprises growing in the soil in a farming season preceding or succeeding the first farming season, at least one plant selected from *Brassica* species, grain species or forage species, harvesting the *Brassica* crop, grain crop or forage crop, obtained in the farming season preceding or succeeding the first farming season, and at least part of plant biomass is left in and/or on the soil.

9. The method according to claim 8, where in the farming season preceding or succeeding the first farming season, seeds of the at least one plant selected from *Brassica* species are doped with a doping composition comprising at least one nitrogen-fixing bacteria, or the seeds of the least one *Brassica* species are not doped.

10. The method according to claim 7, wherein the converting step comprises pretreating the feedstock comprising the *Brassica carinata* seed oil with a method selected from degumming, bleaching, hydrolysis, soap stock splitting, deacidification, alkali neutralization, cold neutralization, micella refining, deodorization, and combinations thereof.

11. The method according to claim 7, wherein the grain species is selected from the group consisting of wheat, rye, barley, oats, rice, sorghum, maize, millet, vegetables, buckwheat, quinoa, fonio, teff, spelt, edible oil seed species, and the forage species is selected from grasses.

12. The method according to claim 7, wherein the doping composition comprises at least one agent capable of inducing nod-factor, and/or wherein the doping composition comprises a germinant, excipient, thickening agent, binder, dispersant, surfactant, polysaccharide, diluent, humectant, carrier and combinations thereof.

13. The method according to claim 7, wherein the converting of the *Brassica* seed oil is carried out by catalytic hydroprocessing, deoxygenation or transesterification.

14. A method for reducing greenhouse gases (GHG) in renewable fuel production, where the method comprises the steps, where,
    seeds of *Brassica carinata* are doped with a doping composition comprising at least one nitrogen-fixing bacteria comprising *Gluconacetobacter* to obtain doped *Brassica carinata* seeds,
    in a first farming season, the doped *Brassica carinata* seeds are planted in soil and a *Brassica carinata* seed crop is harvested,
    the *Brassica carinata* seed crop is treated to obtain *Brassica carinata* seed oil and meal, and
    feedstock comprising the *Brassica carinata* seed oil is converted in a converting step, whereby renewable fuel or renewable fuel components are obtained;
wherein greenhouse gas emission over the course of the method is reduced by over 30% relative to a theoretical maximum greenhouse gas emission of a method wherein a *Brassica carinata* plant, without doping with a nitrogen fixing bacteria, is cultivated in a rotational manner.

15. The method according to claim 14, wherein the method comprises growing in the soil in a farming season preceding or succeeding the first farming season, at least one plant selected from *Brassica* species, grain species or forage species, harvesting the *Brassica* crop, grain crop or forage crop, obtained in the farming season preceding or succeeding the first farming season, and at least part of plant biomass is left in and/or on the soil.

16. The method according to claim 15, where in the farming season preceding or succeeding the first farming season, seeds of the at least one plant selected from *Brassica* species are doped with a doping composition comprising at least one nitrogen-fixing bacteria, or the seeds of the least one *Brassica* species are not doped.

17. The method according to claim 14, wherein the converting step comprises pretreating the feedstock comprising the *Brassica carinata* seed oil with a method selected from degumming, bleaching, hydrolysis, soap stock splitting, deacidification, alkali neutralization, cold neutralization, micella refining, deodorization, and combinations thereof, and/or wherein the pretreatment comprises degumming of the *Brassica carinata* seed oil, where degumming residue is separated from the *Brassica carinata* seed oil.

18. The method according to claim 14, wherein the grain species is selected from the group consisting of wheat, rye, barley, oats, rice, sorghum, maize, millet, vegetables, buckwheat, quinoa, fonio, teff, spelt, edible oil seed species, and the forage species is selected from grasses.

19. The method according to claim 14, wherein the doping composition comprises at least one agent capable of inducing nod-factor, and/or wherein the doping composition comprises at least one of germinant, excipient, thickening agent, binder, dispersant, surfactant, polysaccharide, diluent, humectant, carrier and combinations thereof.

20. The method according to claim 14, wherein the converting of the *Brassica carinata* seed oil is carried out by catalytic hydroprocessing, deoxygenation or transesterification.

21. A method for producing renewable fuels and renewable fuel components, where the method comprises the steps, where,
    seeds of *Brassica carinata* are doped with a doping composition comprising at least one nitrogen-fixing bacteria comprising *Gluconacetobacter* to obtain doped *Brassica carinata* seeds,
    in a first farming season, the doped *Brassica carinata* seeds are planted in soil and a *Brassica carinata* seed crop is harvested,
    in a farming season preceding the first farming season, at least one plant selected from *Brassica* species, grain species or forage species is grown in the soil,
    the *Brassica* crop, grain crop or forage crop obtained in the farming season preceding the first farming season is harvested, and at least part of plant biomass is left in and/or on the soil,
    the *Brassica carinata* seed crop is treated to obtain *Brassica carinata* seed oil and meal, and feedstock comprising the *Brassica carinata* seed oil is converted in a converting step, whereby renewable fuel or renewable fuel components are obtained; wherein greenhouse gas emission over the course of the method is reduced by over 30% relative to a theoretical maximum greenhouse gas emission of a method wherein a *Brassica carinata* plant, without doping with a nitrogen fixing bacteria, is cultivated in a rotational manner.

22. The method according to claim 21, where in the farming season preceding the first farming season, seeds of the at least one plant selected from *Brassica* species are doped with a doping composition comprising at least one nitrogen-fixing bacteria, or the seeds of the least one *Brassica* species are not doped.

23. The method according to claim 1, wherein the doping composition further comprises symbiotic bacteria selected from genera *Terribacillus* spp., *Rhizobium* spp., *Bradyrhizobium* spp., *Pseudomonas* spp. and *Bacillus* spp. in an amount from 0.1 to 50% of the total bacteria.

24. The method according to claim 7, wherein the doping composition further comprises symbiotic bacteria selected from genera *Terribacillus* spp., *Rhizobium* spp., *Bradyrhizobium* spp., *Pseudomonas* spp. and *Bacillus* spp. in an amount from 0.1 to 50% of the total bacteria.

25. The method according to claim 14, wherein the doping composition further comprises symbiotic bacteria selected from genera *Terribacillus* spp., *Rhizobium* spp., *Bradyrhizobium* spp., *Pseudomonas* spp. and *Bacillus* spp. in an amount from 0.1 to 50% of the total bacteria.

26. The method according to claim 1, wherein the converting step comprises pretreating the feedstock comprising the *Brassica carinata* seed oil with degumming of the *Brassica carinata* seed oil, where degumming residue is separated from the *Brassica carinata* seed oil, and wherein at least part of the degumming residue is recycled as fertilizer to the soil.

27. The method according to claim 7, wherein the converting step comprises pretreating the feedstock comprising the *Brassica carinata* seed oil with degumming of the *Brassica carinata* seed oil, where degumming residue is separated from the *Brassica carinata* seed oil, and wherein at least part of the degumming residue is recycled as fertilizer to the soil.

28. The method according to claim 27, wherein at least part of the degumming residue is recycled as fertilizer to the soil.

29. The method according to claim 7, wherein the method comprises growing in the soil in a farming season preceding the first farming season, at least one plant selected from *Brassica* species, grain species or forage species, harvesting the *Brassica* crop, grain crop or forage crop, obtained in the farming season preceding the first farming season, and at least part of plant biomass is left in and/or on the soil.

30. The method according to claim 29, where in the farming season preceding the first farming season, seeds of the at least one plant selected from *Brassica* species are doped with a doping composition comprising at least one nitrogen-fixing bacteria, or the seeds of the least one *Brassica* species are not doped.

31. The method according to claim 14, wherein the method comprises growing in the soil in a farming season preceding the first farming season, at least one plant selected from *Brassica* species, grain species or forage species, harvesting the *Brassica* crop, grain crop or forage crop, obtained in the farming season preceding the first farming season, and at least part of plant biomass is left in and/or on the soil.

32. The method according to claim 31, where in the farming season preceding the first farming season, seeds of the at least one plant selected from *Brassica* species are doped with a doping composition comprising at least one nitrogen-fixing bacteria, or the seeds of the least one *Brassica* species are not doped.

* * * * *